United States Patent [19]
Hearn et al.

[11] Patent Number: 6,048,840
[45] Date of Patent: Apr. 11, 2000

[54] HYPOGLYCAEMIC PEPTIDES

[75] Inventors: Milton Thomas William Hearn, Balwyn; Frank Man-Woon Ng, Vermont South; Victoria Marie Jane Robson, Brighton; Michael Francis O'Donoghue, Warrandyte; Ian David Rae, Mount Waverley, all of Australia

[73] Assignee: Monash University, Victoria, Australia

[21] Appl. No.: 08/221,461

[22] Filed: Apr. 1, 1994

Related U.S. Application Data

[63] Continuation of application No. 07/873,687, Apr. 24, 1992, abandoned, which is a continuation-in-part of application No. 07/477,975, May 17, 1990, abandoned.

[30] Foreign Application Priority Data

Nov. 2, 1987 [AU] Australia ................... PI 5195

[51] Int. Cl.⁷ .............. A61K 38/04; C07K 5/00; C07K 7/00
[52] U.S. Cl. ............. 514/15; 514/16; 514/17; 514/18; 514/19; 530/328; 530/329; 530/330; 530/331; 548/485; 548/544; 548/545
[58] Field of Search ............. 514/15–16, 17, 514/19, 18; 530/328, 329, 330, 331; 548/545, 485

[56] References Cited

U.S. PATENT DOCUMENTS 4,496,521  1/1985  Lewis ........................ 514/12

FOREIGN PATENT DOCUMENTS

87961/75  7/1977  Australia .
8796175   7/1977  Australia .
8904323   5/1989  WIPO .

OTHER PUBLICATIONS

Thompson, et al, Drug, Design and Discovery, vol. 13, pp. 52–72, 1995 (Exhibit C).
Chemical Abstract, vol. 112, 1990.
Geiger et al., Journal of Biol. Chem., 262:785–794 (1987).
Ball et al., Journal of Molecular Recognition, 3(2):55–64 (1990).
CAPLUS on STN database; No. 1981:587631. Fujino et al. "The 4=methoxy-2, 6–dimethylbenzenesulfonyl (Mds): a new protecting group of guanidino functin in peptdie synthesis" 1980.
Murray et al., "Metabolism of a Synthetic L–Isoaspartal–Containing Hexapeptide in Erythrocyte Extracts", Journal of Biological Chemistry, vol. 261, No. 1, pp. 308–312, Jan. 5, 1986.
Kimura et al., "Strategy for Sythesis of Large Peptides: An Application to the Total Sythesis of Human Parathyroid Hormone [hPTH (1–84)]", Biopolymers, vol. 20, No. 9, pp. 1823–1832 (abstract only), 1981.
Ondetti et al., Biochemistry 1968, 7 4069–4075.
Pullin et al., Int. J. Peptide Protein Res., 1981 18 318–323.
Perseo et al., Int. J. Peptide Protein Res., 1986 27 51–60.
Chemical Abstracts, 1985 102 No. 167166v.
Chemical Abstracts, 1980 92 No. 198744m.
Partial European Search Report.

*Primary Examiner*—Cecilia J. Tsang
*Assistant Examiner*—Anish Gupta
*Attorney, Agent, or Firm*—Finnegan, Henderson, Farabow, Garrett & Dunner, L.L.P.

[57] ABSTRACT

This invention relates to novel insulin-potentiating hypoglycaemic compounds.

42 Claims, 26 Drawing Sheets

INFRARED SPECTRA OF PEP (6-13) α-FORM

α-FORM

FAB-MS

β-IMIDE

HYPOGLYCAEMIC PEPTIDES

This application is a continuation application of Ser. No. 07/873,687 filed Apr. 24, 1992 now abandoned, which is a continuation-in-part of application Ser. No. 07/477,975 filed May 17, 1990, now abandoned.

This invention relates to methods of controlling blood glucose levels, and in particular to novel compounds with hypoglycaemic activity and to processes for producing these compounds.

BACKGROUND OF THE INVENTION

The principal factor controlling blood glucose levels is the hormone insulin. Diabetes may result either from insufficient production of insulin or from resistance to the action of circulating insulin.

It has been suggested that a peptide fragment of human growth hormone (hGH), derived from enzymic digestion of pituitary, can counter the effects of natural inhibitors of insulin (Australian patent application no. 87961/75 by Choay S. A.). This α-peptide chain, having sequence leu-ser-arg-leu-phe-asp-asn-ala, is comprised of amino acids all of which have the L configuration.

This peptide, equivalent to hGH 6-13, was stated to be able to counteract the inhibition of insulin by somantin, a degradation product of growth hormone, and was thought to potentiate the effects of insulin, to induce synthesis of insulin receptor sites on cells, and to sensitize β cells in the islets of Langerhans to glucose.

However, it has subsequently been found that the peptide disclosed by Choay does not have these activities. In fact, inconsistency in demonstrating the claimed biological activities, due to the absence of detailed knowledge of the precise conformational structure of the active substance, prevented further development and validation of the original work by Bornstein and co-workers, inventors in respect of 879661/75, and this application lapsed.

Synthesis of peptides has been carried out on a small scale since the initial work of Emil Fischer in 1900 and became a commonplace technique in biochemistry in the 1950s, when solution phase methods were used. The development of solid phase peptide synthetic techniques by Merrifield in the late 1960s resulted in an explosive expansion of this work, and it is now regarded as a routine technique in biochemistry. The peptides which can be constructed using these techniques may have the same sequences as naturally occurring peptides; sequences which are modified from the natural sequence at one or more points, or are entirely non-natural; sequences which incorporate amino acids which do not occur naturally in living organisms, including D-amino acids, ε-amino acids, and non-naturally occurring α-amino acids; and sequences which incorporate both amino acids and other chemical structures which are not themselves amino acids. In other words, these techniques provide the ability to modify or construct sequences at will; by these means, the structural requirements of peptides, in particular their 3-dimensional structures, which are necessary for their proper functioning have been explored.

Part of these explorations commonly includes the substitution of amino acids in a given sequence either by other amino acids, which may be naturally-occurring or non-naturally-occurring, or by analogous chemical structures; the only requirement is that such analogous chemical structures must be able to be attached to the growing peptide chain, and the analogues are usually chosen so that they can be used in conventional solid phase synthetic methods. It is well known that if such a substitution is successful with one peptide, it is likely to succeed in other situations, including other peptide sequences. The effect of a given substitution can now be predicted on a theoretical basis in small peptides, based on a limited number of experiments.

We have now surprisingly found that although α-peptide chains equivalent to hGH 6-13 are biologically inactive, peptides in which residues equivalent to $asp_{11}$ and $asn_{12}$ of the hGH sequence form a β-imide group do have biological activity. This cyclic imide group, which forms a structure known in the art as a Type II' β-turn, forms a characteristic 3-dimensional structure which we believe to be essential for activity of the peptide. The aspartimido group is well known to be associated with a Type II' β-turn.

We have now prepared a family of novel β-imide linked L-aspartyl-L-asparaginyl peptides wherein the general structure of the peptide may additionally involve between 2 and 6 other α-amino acid residues of either the D- or L-stereochemical form, or involve other non α-amino acid substitutions at positions 1 or 6 to 12.

Furthermore, the in vitro and in vivo properties of these β-imido-L-aspartyl-L-asparaginyl peptides as potent hypoglycaemic agents with functional capabilities of potentiating insulin action are demonstrated. In this application we describe (i) the synthesis of these peptides via solid and solution phase peptide synthetic protocols; (ii) the purification and structural characterization of these peptides; (iii) the in vitro evaluation of these peptides in various biological assay systems; (iv) the evaluation of these peptides in lowering blood glucose levels in vivo.

(a) Electrophoresis was performed at pH 6.5 for 1 h at 1.5 kV.

(b) Electrophoresis was performed at pH 3.0 for 2.5 h at 1.5 kV.

Figure 8A:
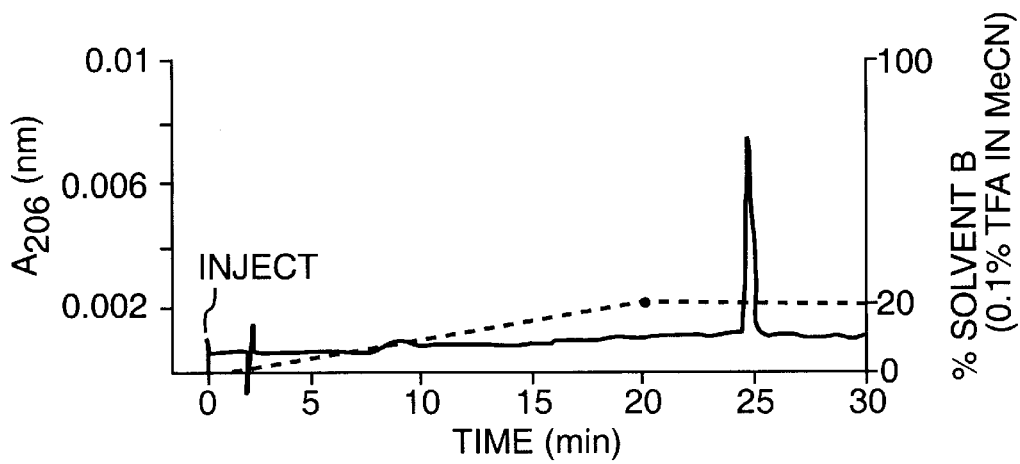
Figure 8B:
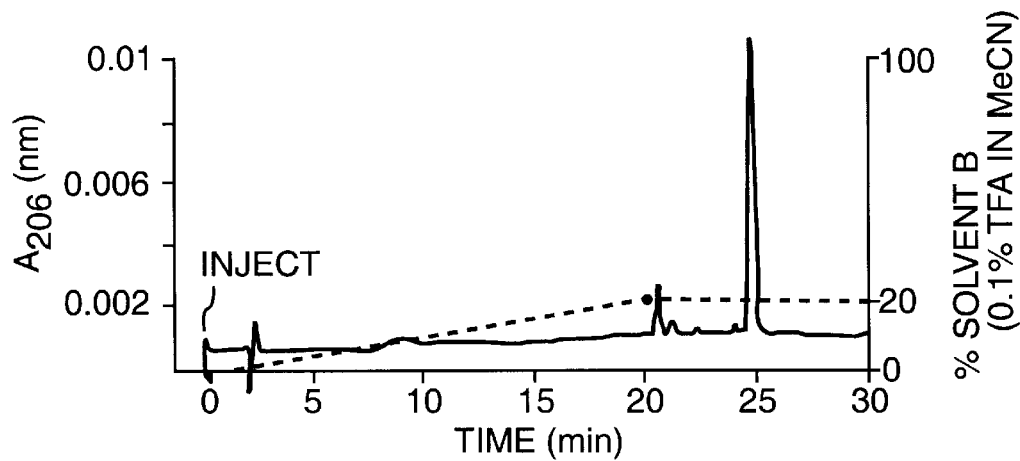
Figure 8C:
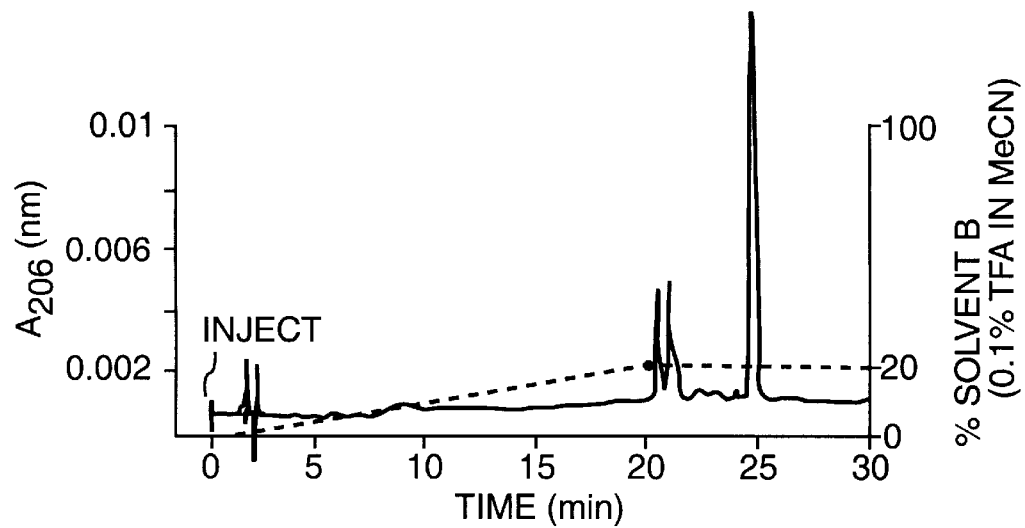
Figure 9A:
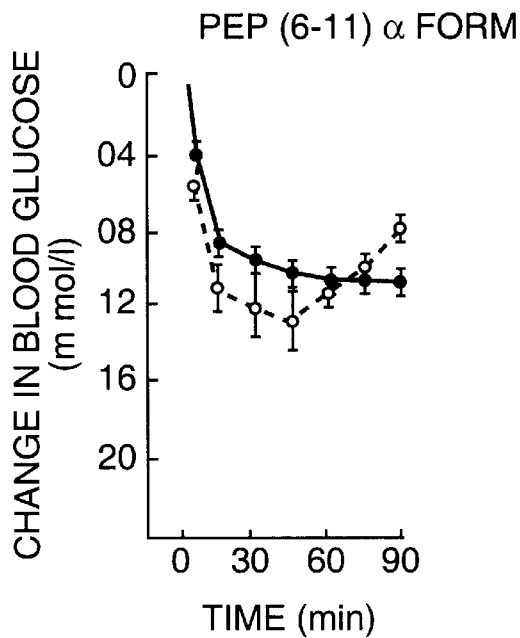
Figure 9B:
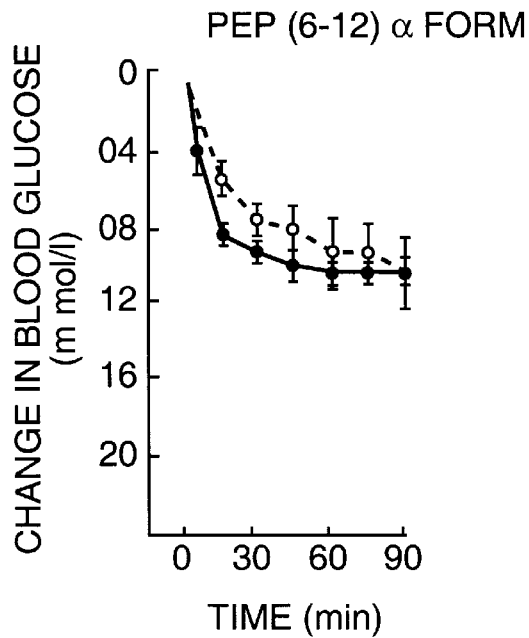
Figure 9C:
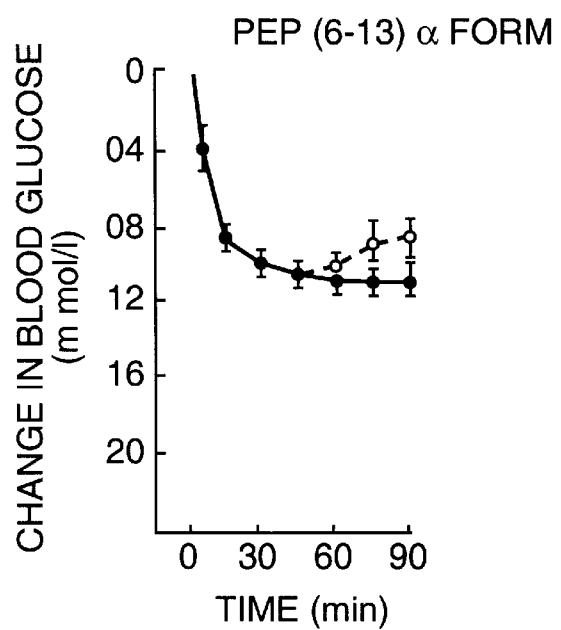
Figure 9D:
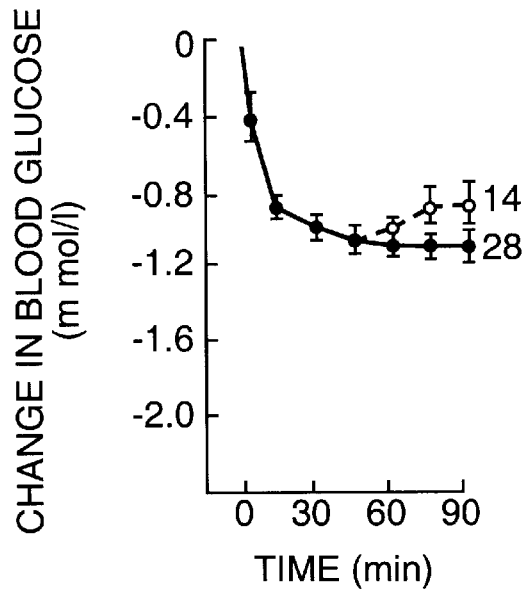
Figure 9E:
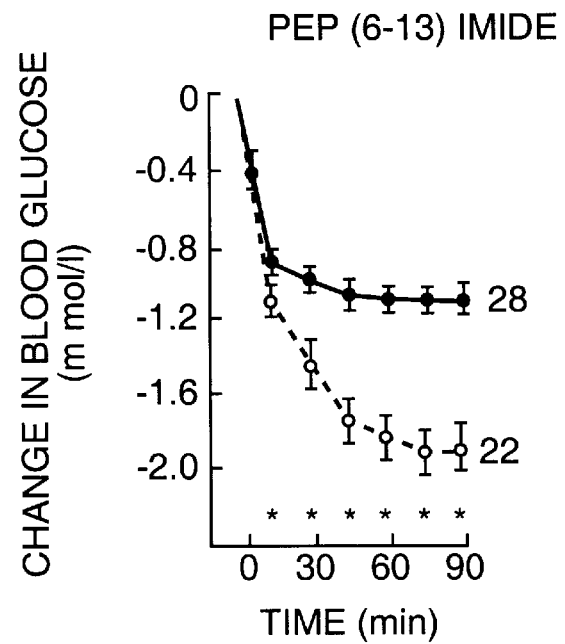
Figure 9F:
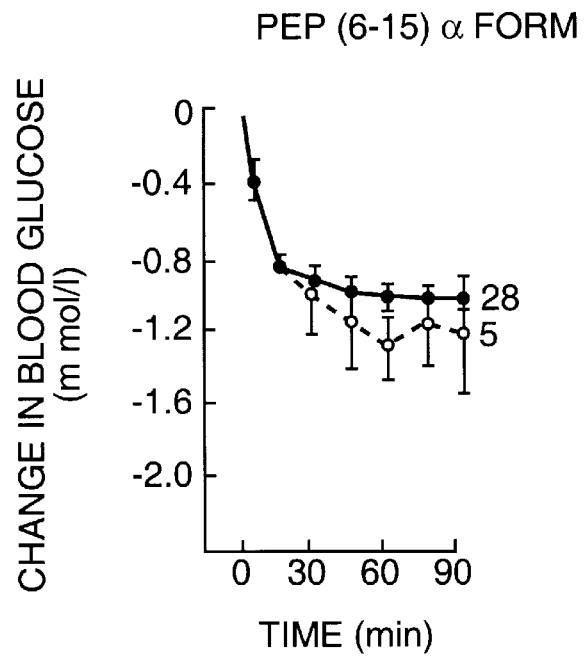
Figure 9G:
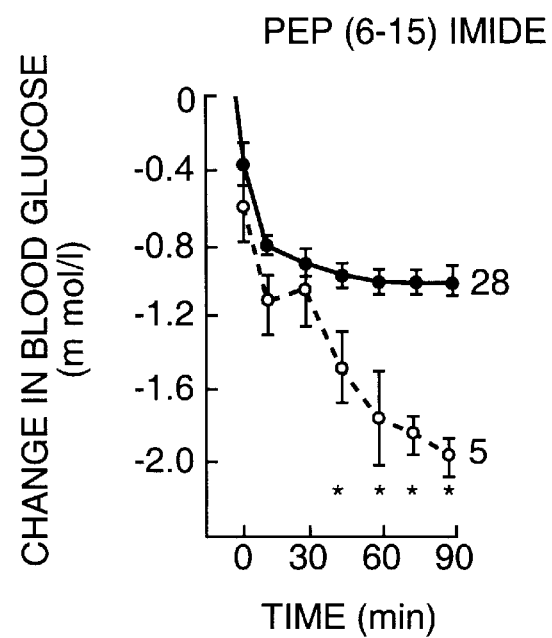
Figure 9H:
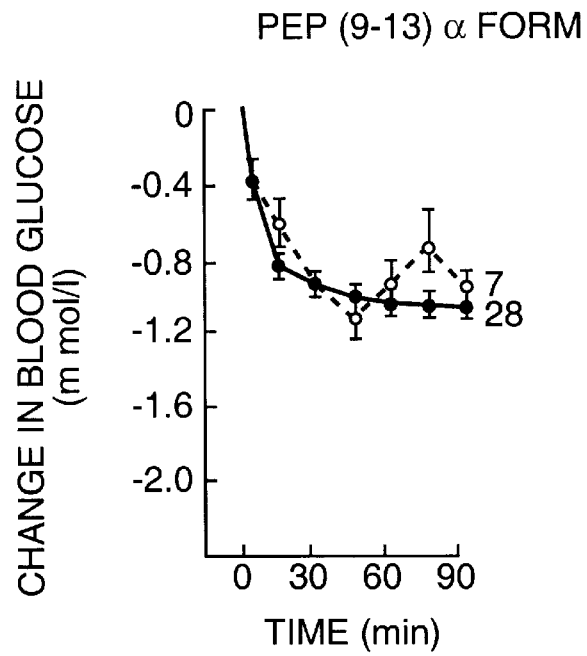
Figure 9I:
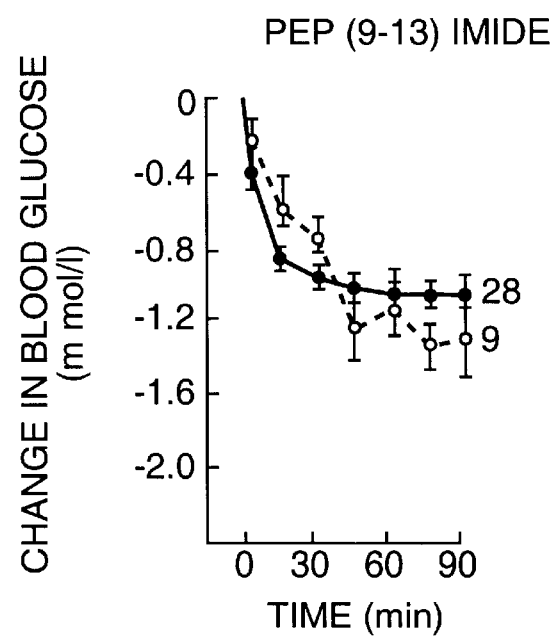
Figure 9J:
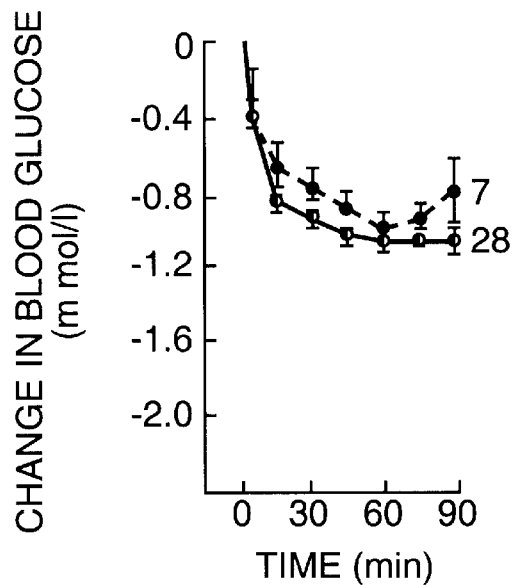
Figure 9K:
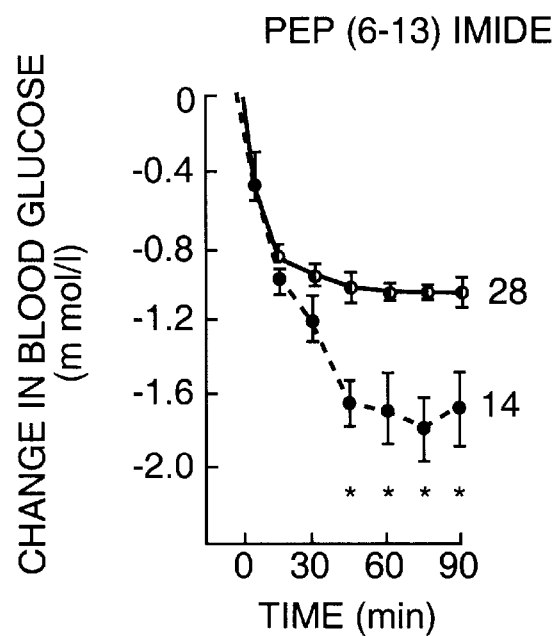
Figure 9L:
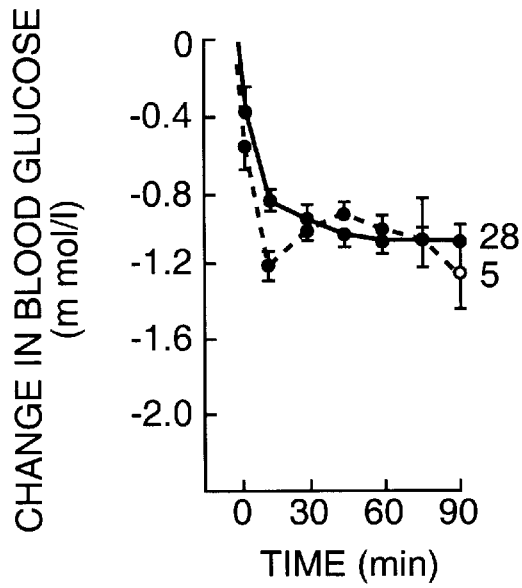
Figure 9M:
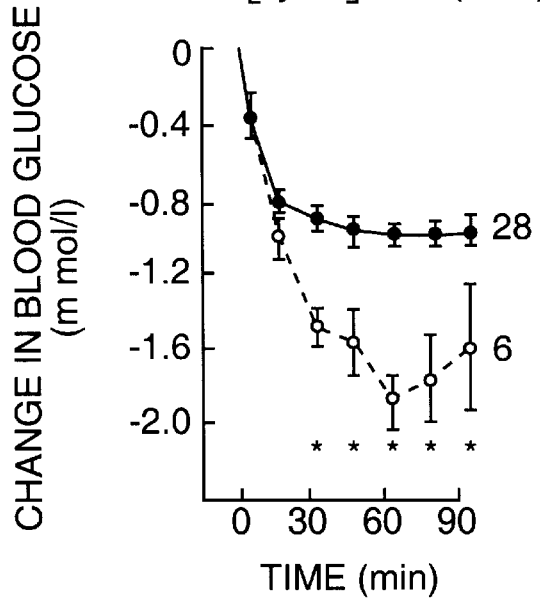
Figure 9N:
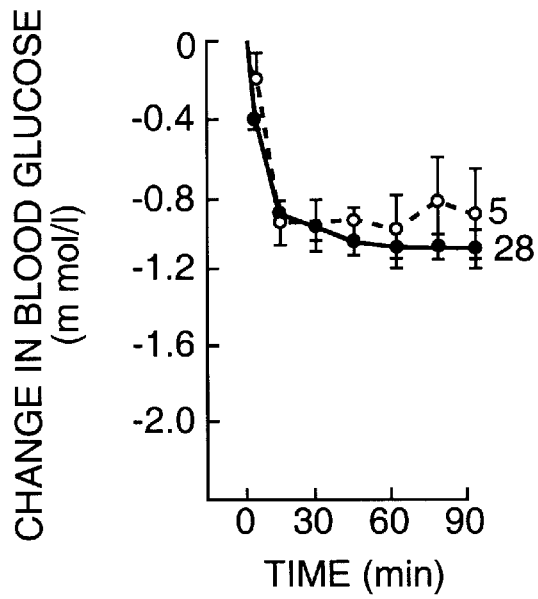
Figure 9O:
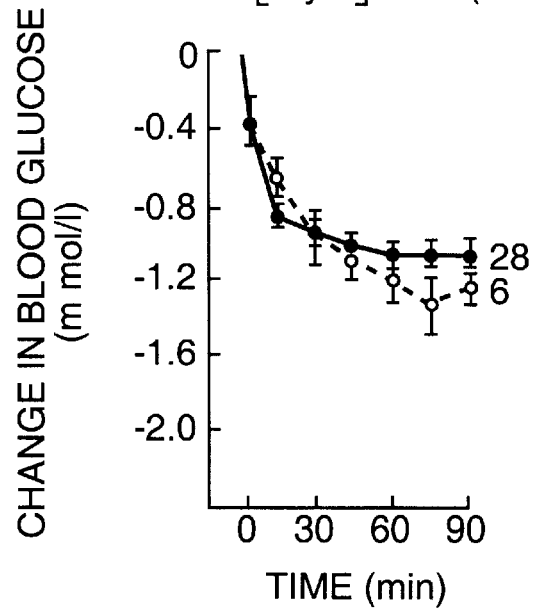
Figure 9P:
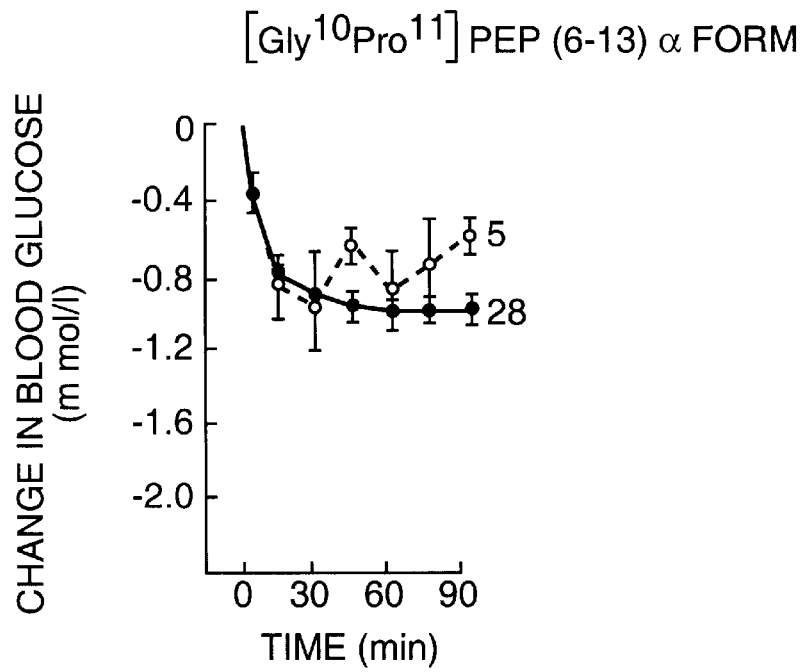
Figure 9Q:
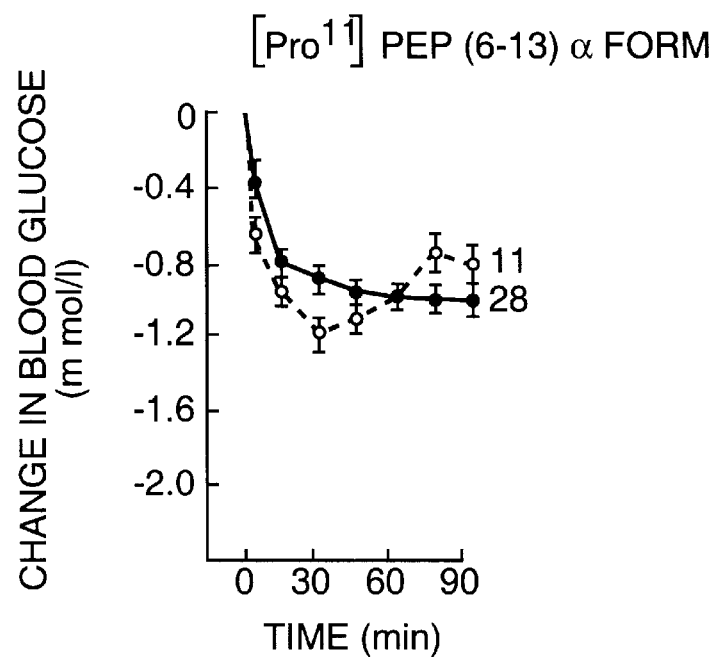
Figure 10A:
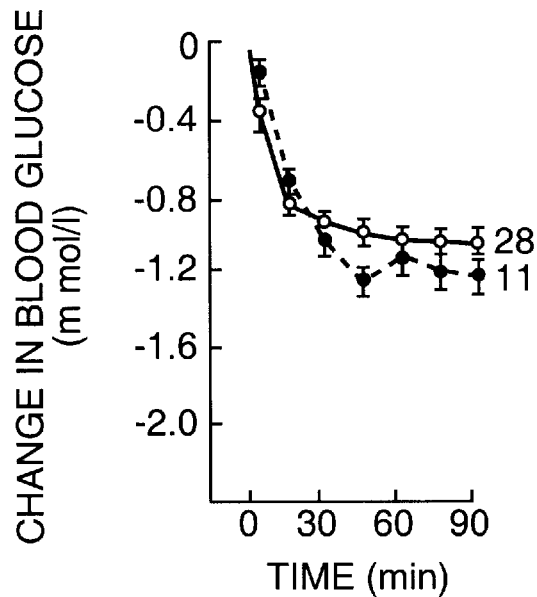
Figure 10B:
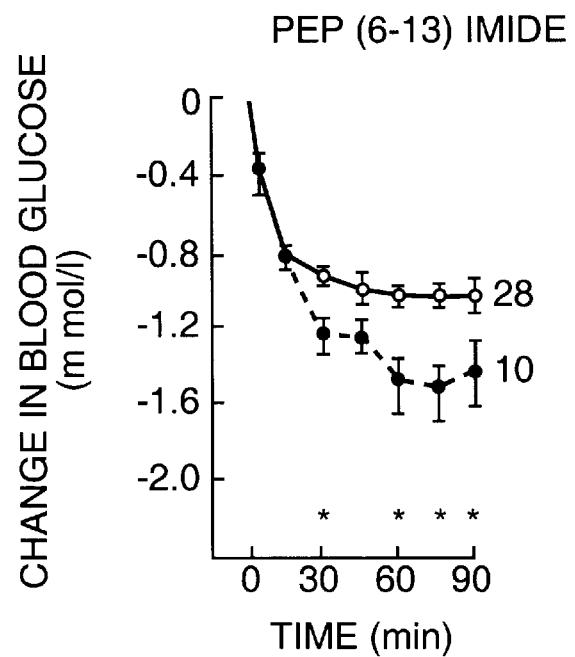
Figure 10C:
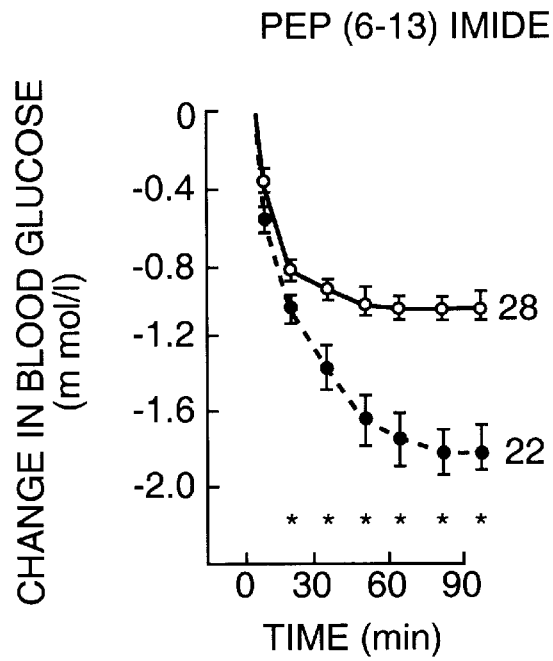
Figure 10D:
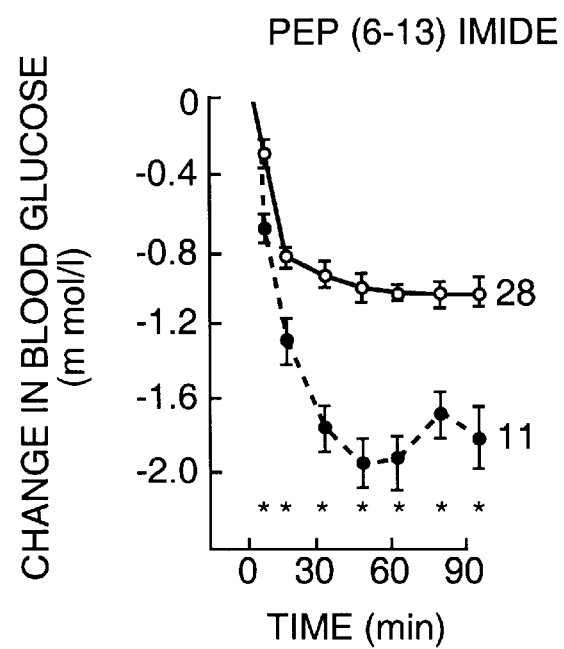

Peptides were detected by spraying with ninhydrin;

FIG. 8 represents HPLC chromatograms or synthetic Pep (6-13) peptides using a shallow gradient (0%–20% Solvent B over 20 min).

(a) Injection of purified synthetic Pep (6-13) β-aspartimido form I, active.

(b) Injection of partly hydrolysed synthetic Pep (6-13) β-aspartimido form I.

Figure 11:
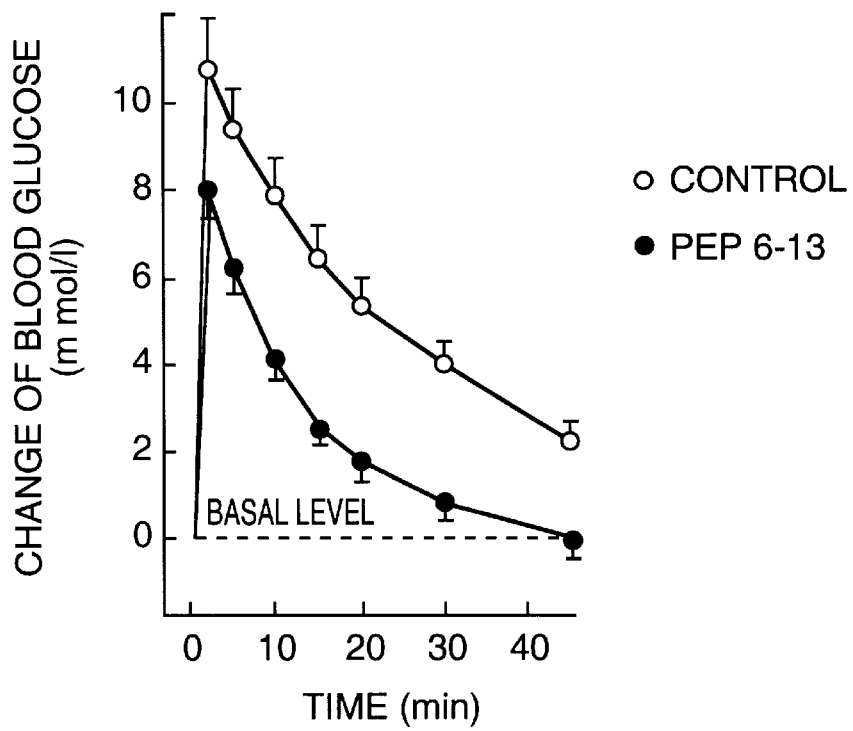
Figure 12A:
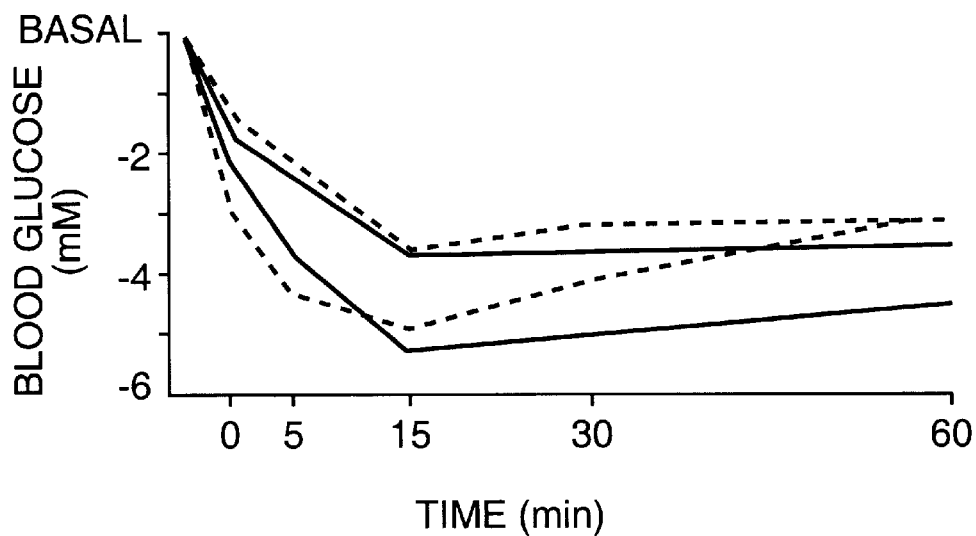
Figure 12B:
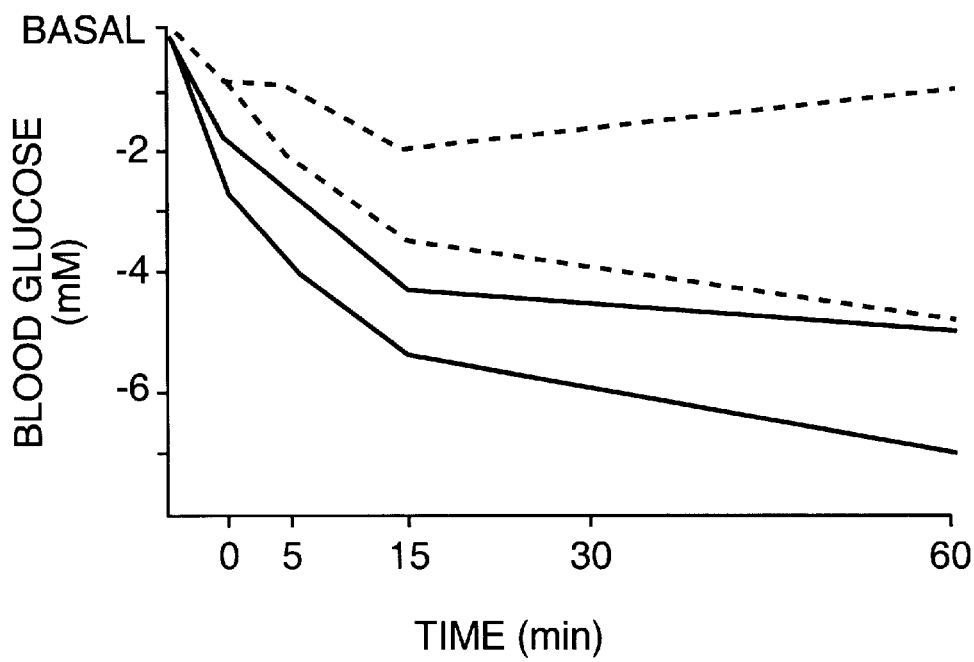
Figure 13A:
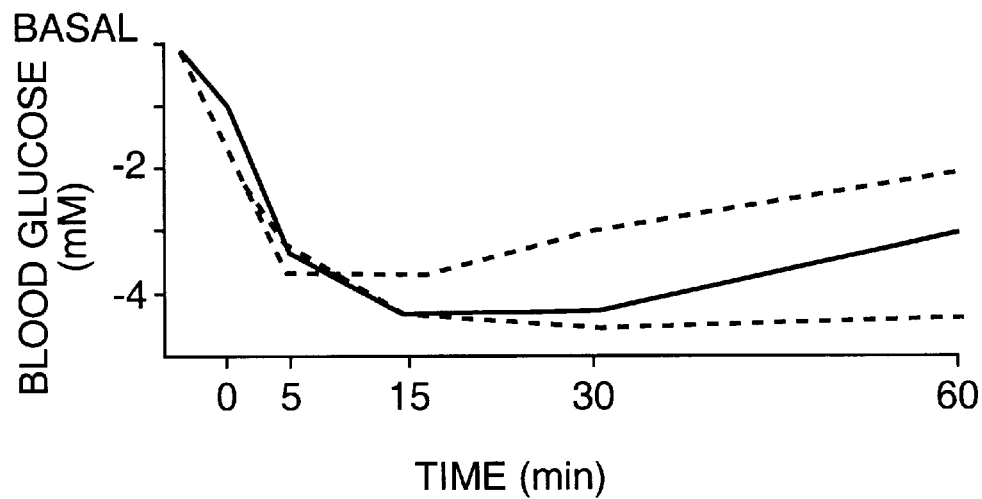
Figure 13B:
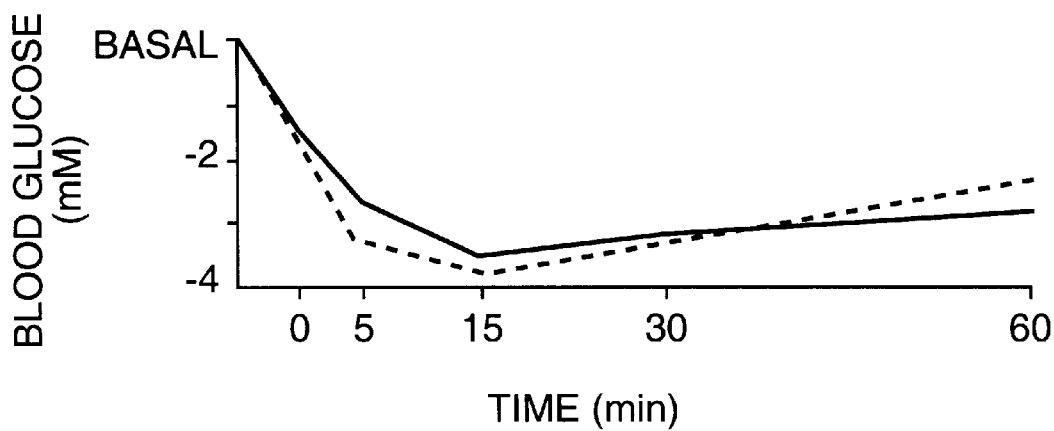
Figure 13C:
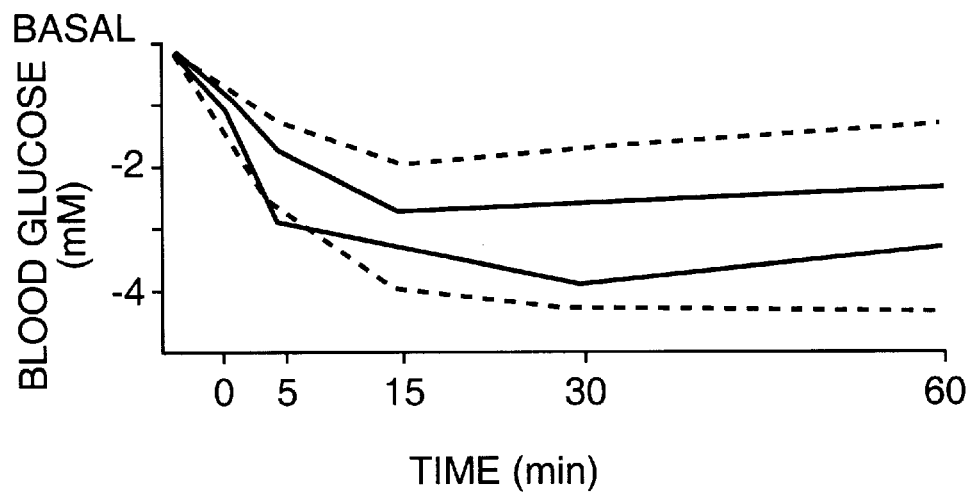
Figure 13D:
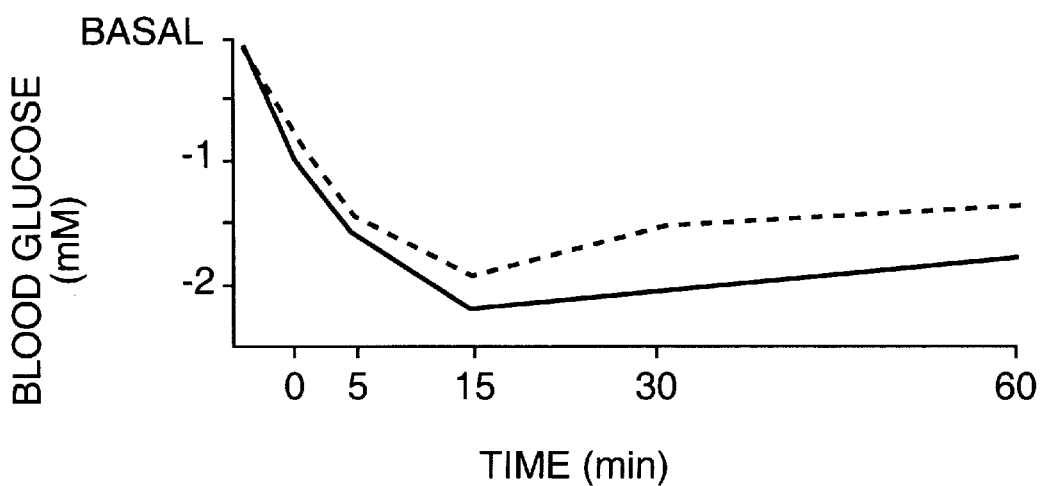

(c) Simultaneous injection of inactive synthetic Pep (6-13) α-form peptide and active β-aspartimido form I Pep (6-13) peptide α-form;

FIG. 9 represents the change in blood glucose level in rats following injection of various synthetic inactive α form and active β-aspartimido forms of peptides according to the invention;

FIG. 10 represents the effect of various doses of Pep (6-13) β imide during intravenous insulin sensitivity tests on normal rats;

FIG. 11 represents the effect of Pep (6-13) on glucose tolerance tests in normal rats;

FIG. 12 represents in vivo testing of Pep (6-13) (Asn$^{11}$Asp$^{12}$) (FIG. 11a) and Pep 6-13 (Asp$^{12}$) (FIG. 11b) for insulin-potentiating activity on untreated female mice. The dotted lines represent control animals (injected with 0.2 ml of saline) in each case. The unbroken lines represent test The unbroken lines represents the mean fall in blood glucose animals (injected with 2.4 mg/kg of peptide in 0.2 ml of saline). Insulin was injected at $t_o$;

FIG. 13 represents in vivo testing of peptides for insulin-potentiating activity on untreated and treated male mice. The dotted line represents the mean fall in blood glucose for control animals (injected with 0.2 ml of saline). The unbroken line represents the mean fall in blood glucose for test animals, injected with 2.3 mg/kg of peptide in 0.2 ml of saline, except for (a), in which the dose was 2.4 mg/kg.

Figure 14:
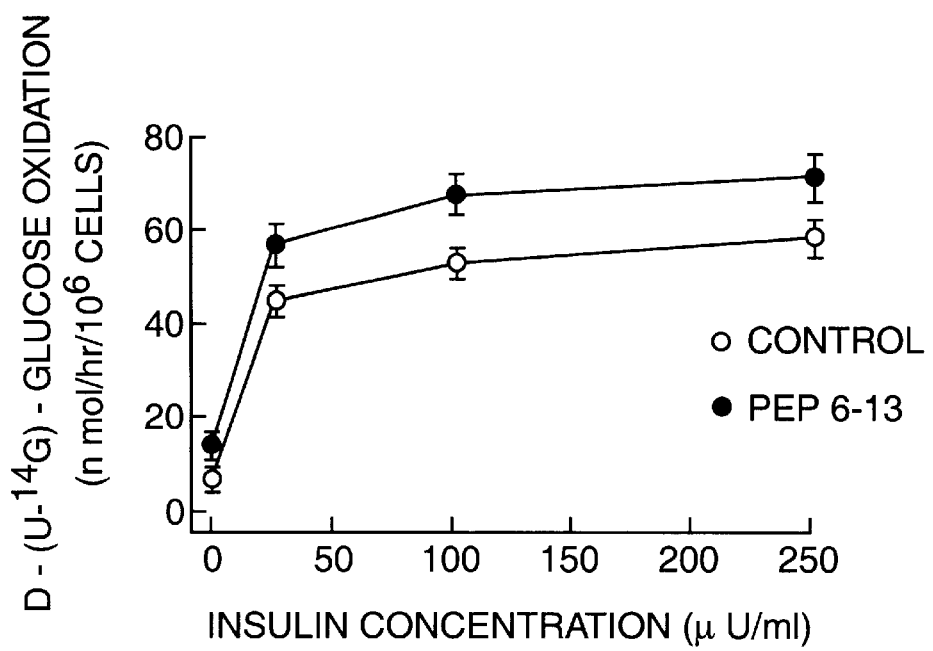
Figure 15:
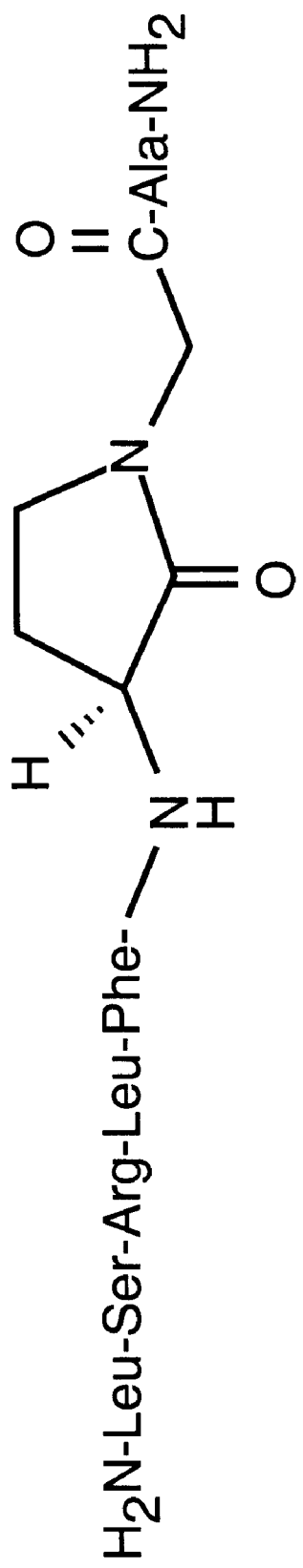
Figure 16:
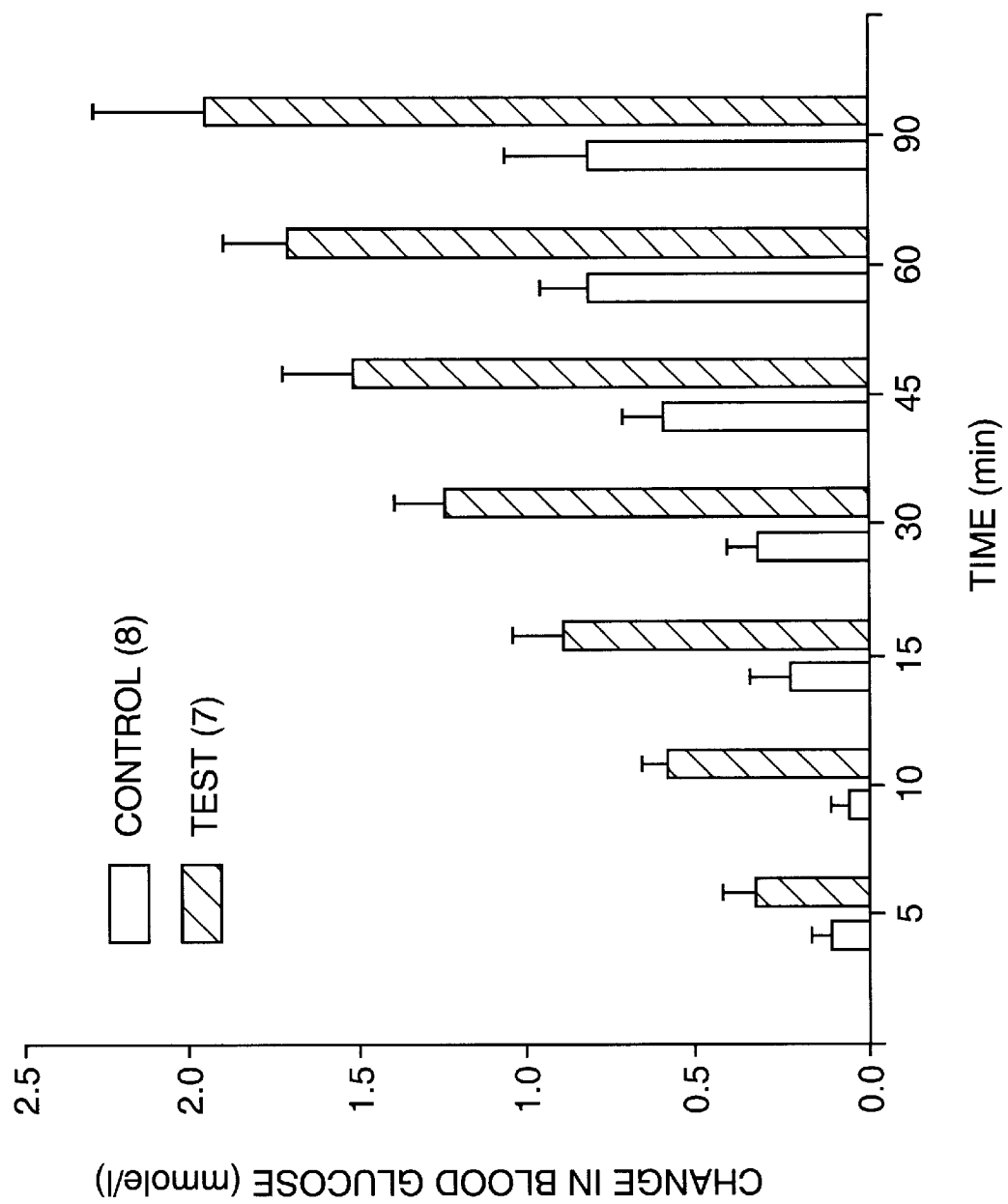
Figure 17:
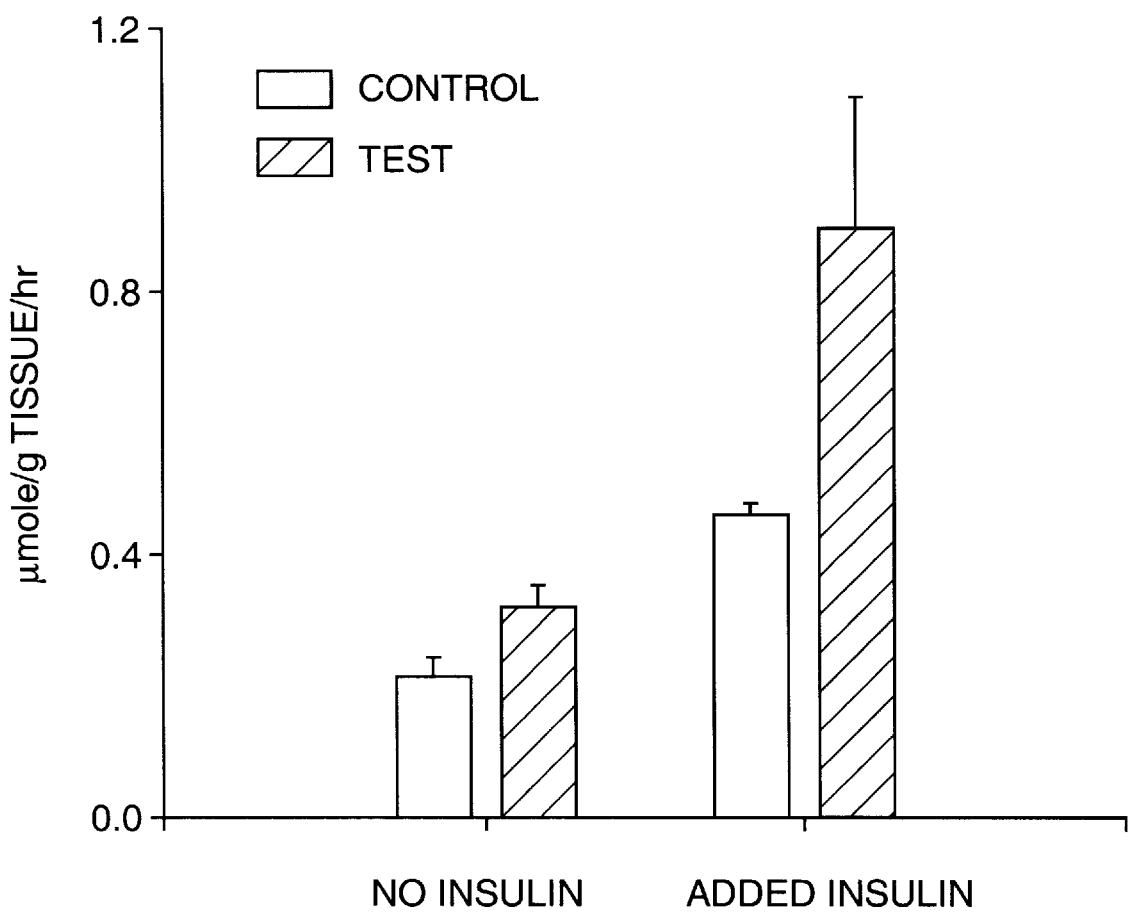

(a) Pep 6-13 (Gln$^{11}$Asp$^{12}$), untreated (b) Pep 6-13 (Gln$^{11}$Asp$^{12}$), treated (c) Pep 6-13 (Asn$^{11}$Asp$^{12}$), treated (d) Pep 6-13 (Asp$^{12}$), treated Insulin was injected at $t_o$;

FIG. 14 represents the in vitro effect of Pep (6-13) β imide on glucose oxidation in isolated rat adipocytes in the absence and in the presence of various levels of insulin;

FIG. 15 represents shows the structure of a peptide according to the invention in which a γ-lactam group is used instead of an aspartimido group (γ-lactam$^{11}$l-hGH[6-13]);

FIG. 16 represents the in vivo effect of γ-lactam$^{11}$-hGH [6-13]) on blood glucose levels during intravenous insulin tolerance tests; and FIG. 17 represents the in vivo effect of γ-lactam$^{11}$-hGH [6-13]) on glucose incorporation into glycogen in diaphragm muscles.

SUMMARY OF THE INVENTION

According to one aspect of the present invention there is provided a compound of general formula I:

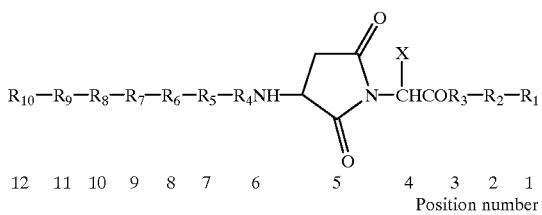

wherein X is hydrogen, $CH_2CONH_2$ or $-CH_2CH_2CONH_2$;
each of $R_1$, $R_2$ and $R_3$ is an L-α-amino acid, a δ-amino acid or an ε-amino acid;

$R_4$ is an L or D α-amino acid, a δ-amino acid or an ε-amino acid; and each of $R_5$ to $R_{10}$ is hydrogen or an L or D α-amino acid, a δ-amino acid or an ε-amino acid, or a pharmaceutically acceptable salt thereof.

Preferably $R_5$ is a L or D α-amino acid, a δ-amino acid or an ε-amino acid.

Preferably each of $R_1$, $R_2$ and $R_3$ is selected from the group consisting of alanine, glycine and phenylalanine.

Preferably $R_4$ is a hydrophobic amino acid; more preferably $R_4$ is selected from the group consisting of L-phenylalanine, L-tyrosine, L-tryptophan and L-histidine.

Preferably $R_5$ is a hydrophobic amino acid; more preferably $R_5$ is selected from the group consisting of L- or D- leucine, isoleucine and histidine.

$R_6$ is a basic amino acid, and is preferably selected from the group consisting of L- or D-arginine, lysine, and histidine.

$R_7$ is preferably a substantially hydrophobic amino acid, and is preferably selected from the group consisting of L- or D- serine, leucine and isoleucine.

$R_8$ is preferably selected from the group consisting of L- or D- leucine, phenylalanine, proline or isoleucine, an ε-amino acid such as 6-aminohexanoic acid, 4-aminocyclohexane-1-carboxylic acid or similar amino acids.

Each of $R_9$ and $R_{10}$ is preferably a substantially hydrophobic amino acid, and is most preferably selected from the group consisting of L- or D- leucine, phenylalanine, proline, isoleucine or tyrosine.

$R_8$, $R_9$ or $R_{10}$ may optionally be coupled to $R_1$ via a bifunctional agent such as 6-aminohexanoic acid.

The amino acids may optionally have side chain substituents.

$R_1$, $R_2$, $R_8$, $R_9$, or $R_{10}$ may be absent from the peptide, allowing coupling between C-terminal and N-terminal amino acids via a bifunctional agent such as 6-aminohexanoic acid.

$R_6$ is equivalent in terms of sequence alignment to residue 8 of human growth hormone.

Figure 1:
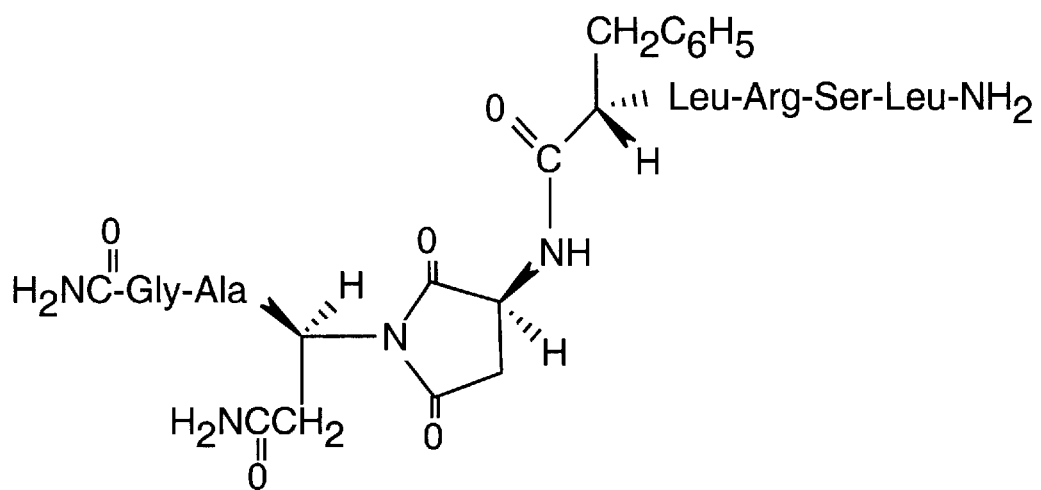
FIG. 1 represents a stereochemical view of a representative peptide according to the invention.
Figure 2:
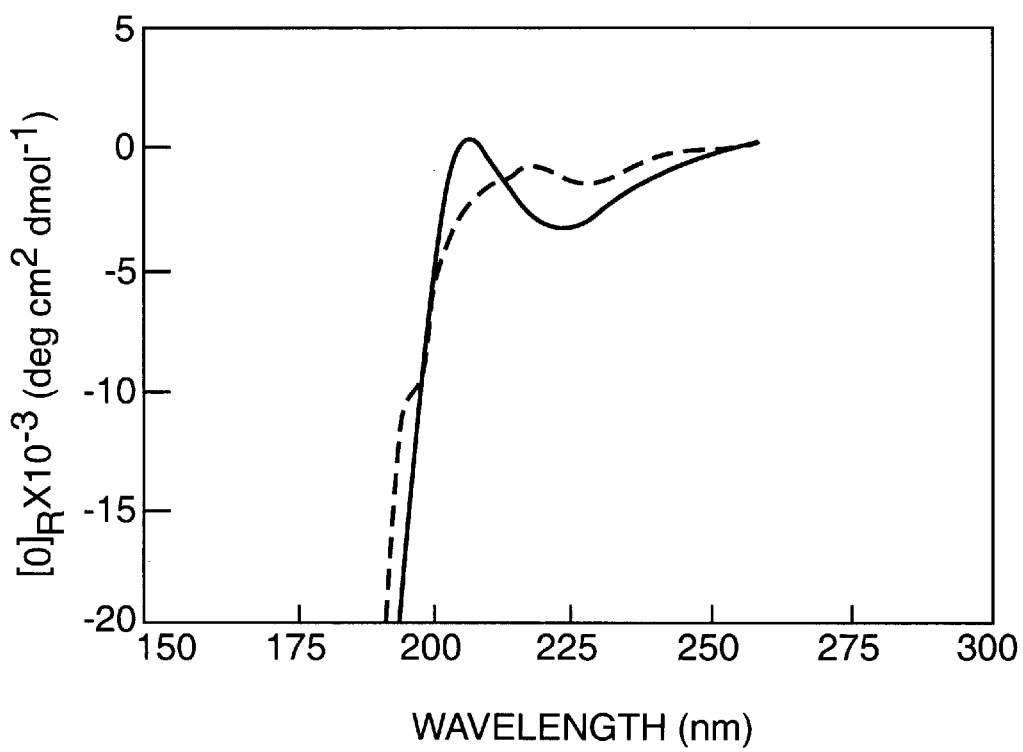
FIG. 2 represents far ultraviolet circular dichroic spectra for synthetic peptide Pep (6-13) β-aspartimido form I(__) and synthetic peptide Pep (6-13) α-form (-----). Spectra recorded in water at 21° C. using 1 mg/ml solutions in 0.1 mm cells.
Figure 3:
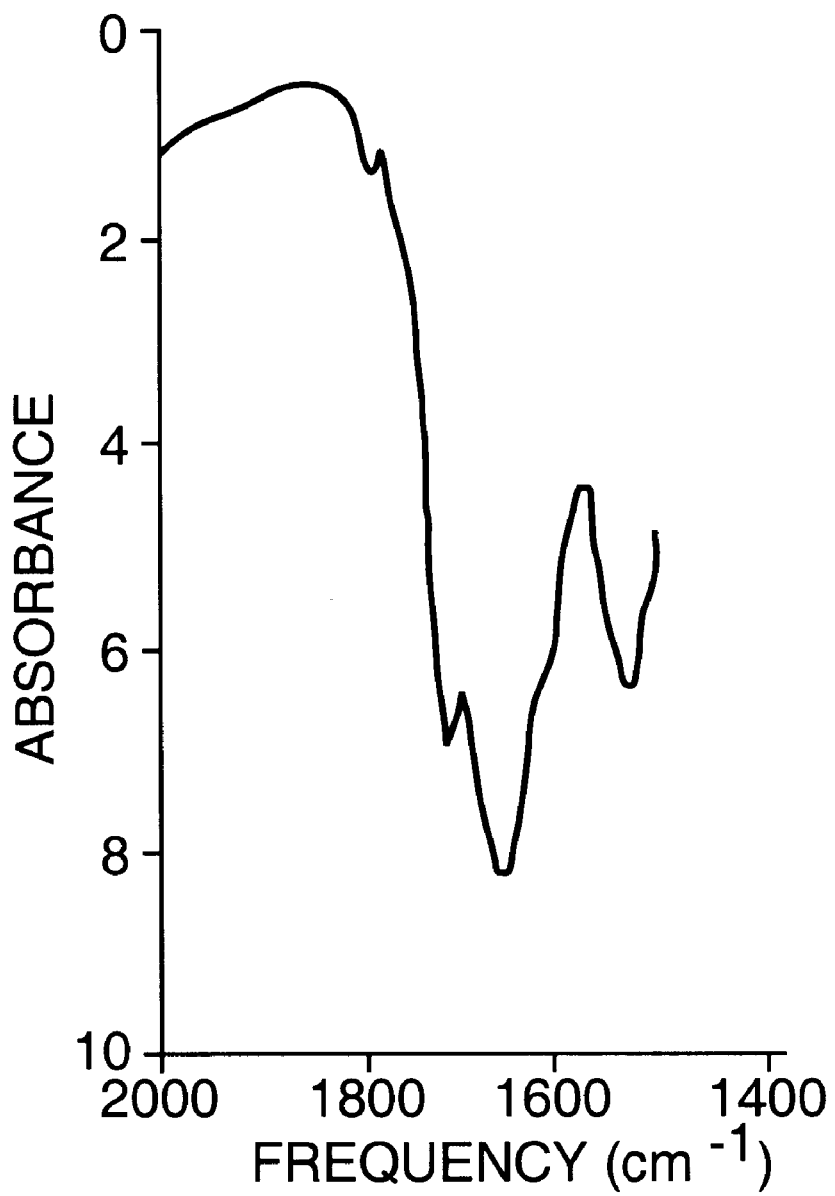
FIG. 3 represents infra-red spectrum for active synthetic peptide (6-13) β-aspartimido form I. The spectrum was measured between 2000–1500 $cm^{-1}$ after the peptide sample (ca. 5 mg) Was pressed into a KBr disc.
Figure 4A:
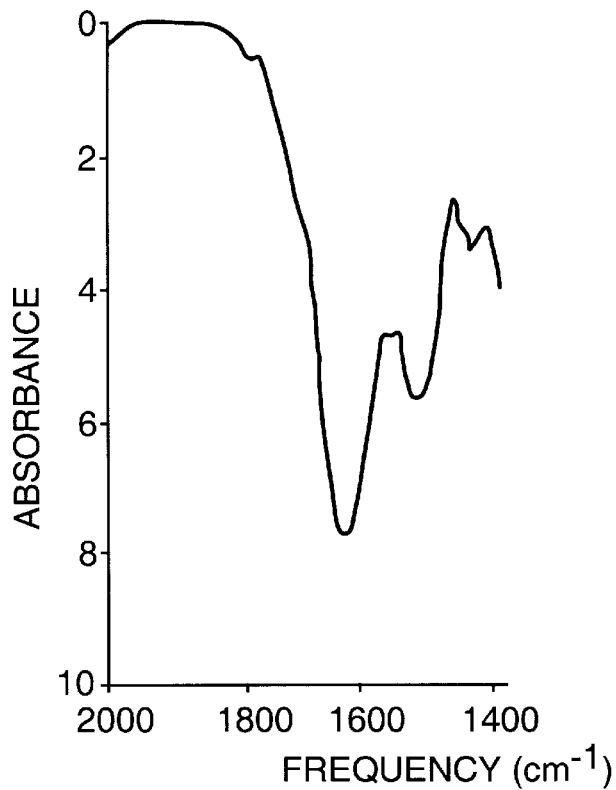
FIG. 4 represents infra-red spectrum for synthetic peptide Pep (6-13) α-form, inactive. The spectra were measured between 200–1500 $cm^{-1}$. (a) the sample (ca. 5 mg) of peptide was pressed into a KBr disc. (b) the sample (ca. 5 mg) of peptide was saturated with Nujol to form a mull.
Figure 4B:
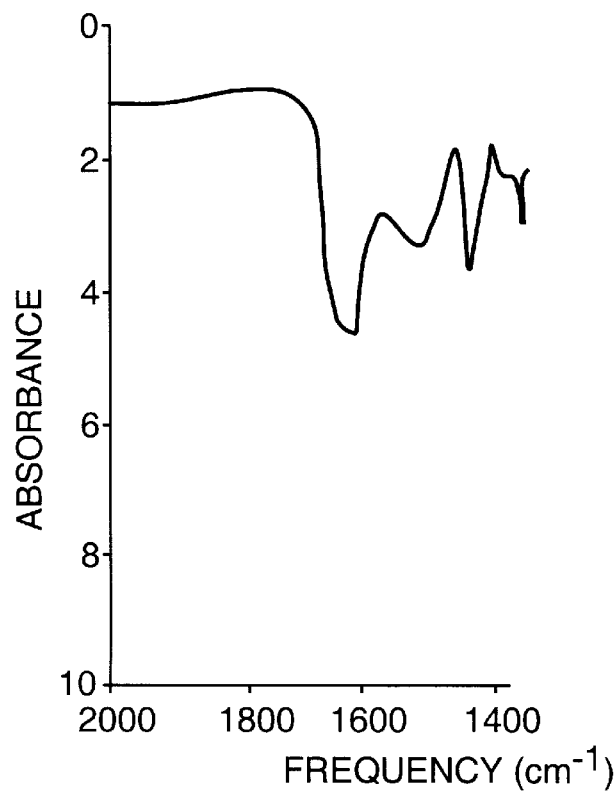
Figure 5A:
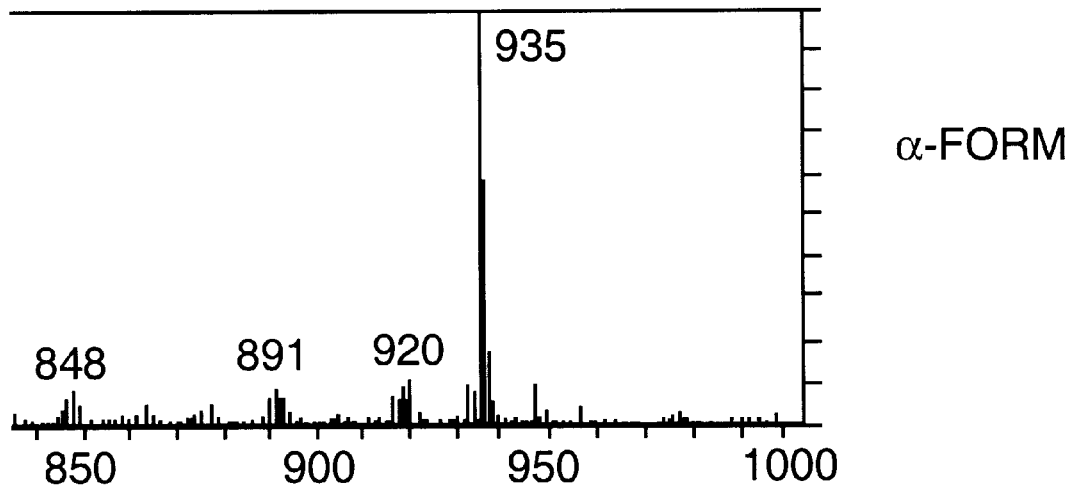
FIG. 5 represents fast atom bombardment (FAB) mass spectrometric spectra of the synthetic peptides active β-aspartimido form I Pep (6-13) and inactive α-form Pep (6-13)
Figure 5B:
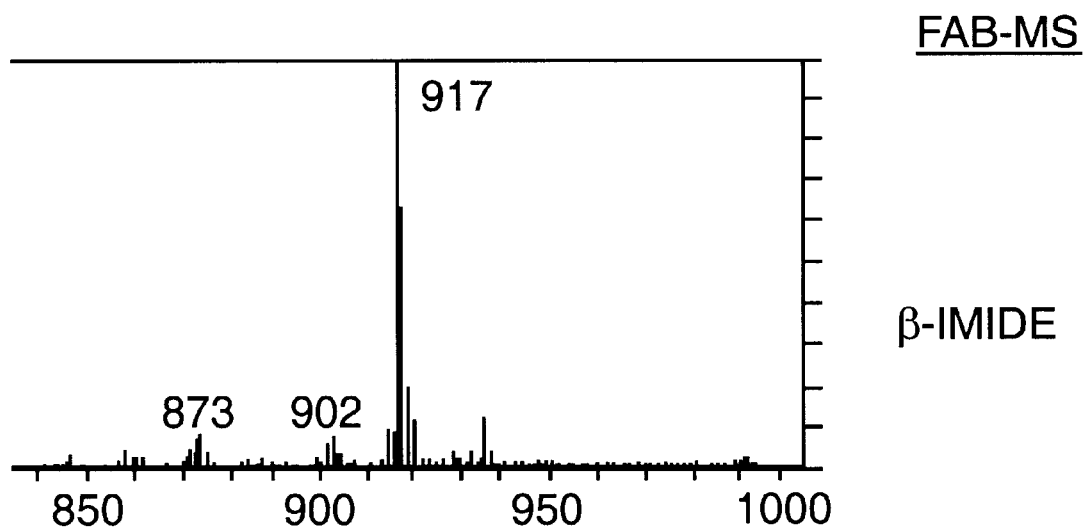
Figure 6A:
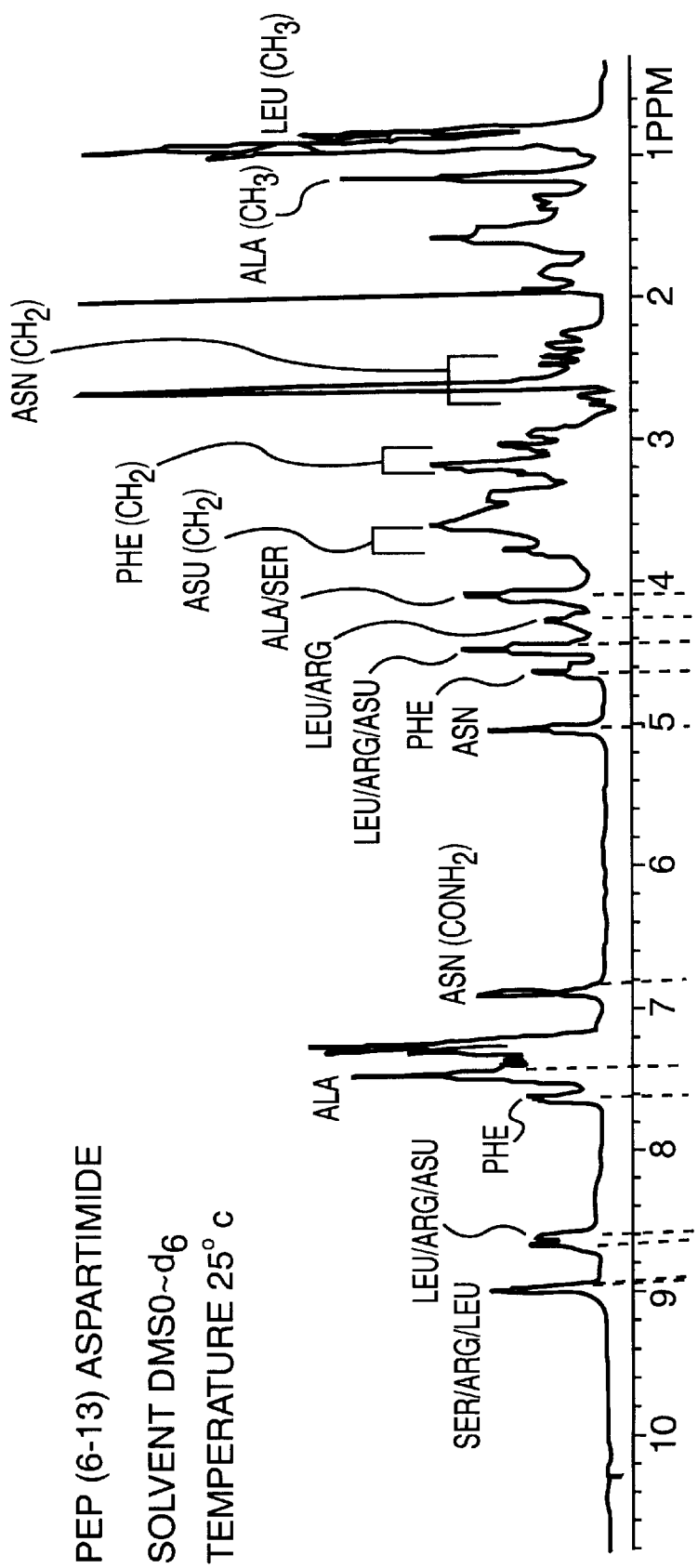
FIG. 6 represents $^1H$ N.M.R. spectrum of active β-aspartimido form I synthetic peptide Pep (6-13)
Figure 6B:
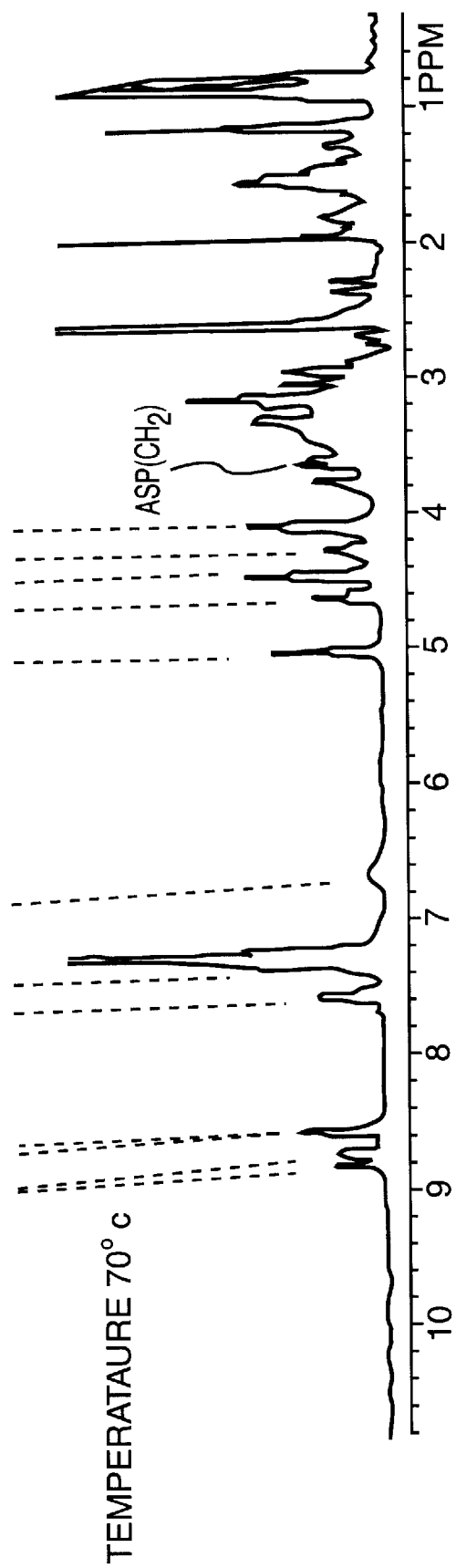

The cyclic imide structure as shown in general Formula I is essential for activity. Activity increases with chain length up to 8 residues. A stereochemical view of a representative peptide is shown in FIG. 1.

The peptide according to the invention forms an amphipathic helix structure having a fluid hydrophobic face and a second face carrying an exposed imide group.

It will be apparent to persons skilled in the art that pharmacologically active analogues and derivatives of the compound of general formula I are within the scope of the invention, e.g. o-, m-, or p-aminobenzoic acid or α- or δ-lactams in place of the aspartimide ring.

It will be apparent to persons skilled in the art that pharmacologically active analogues and derivatives of the compound of general Formula I are within the scope of the invention, e.g., o-, m,-, or p-aminobenzoic acid or α- or β-lactams in place of the aspartimide ring.

For example, ν- or δ-lactam groups may be used instead of β-aspartimido groups (Freidinger R. M. et al.; Int. J. Peptide Protein Research; 1984 23 142–150; Freidinger, R. M. et al., Peptide Synthesis, Structure and Function Ed. D. Rich and E. Gross, 1981 673–683; Freidinger, R. M. et al., Science, 1980 656–658; Capassio, S. et al., Int. J. Peptide Protein Research, 1984 23 248–255); other groups may also be used to provide the requisite Type II' β-turn. For example, if one of the carbonyl groups is removed from the β-lactam structure, the β-alanine moiety results; this β-alanine structure also results in a break in the α-helix. Aminobenzoic acid is a fully constrained analogue of β-alanine. A hierarchy of activity may be predicted, as follows:

aspartimide>lactam>aminobenzoic acid.

The present inventors have made peptides of general formula I with these substitutions, and have found that activity is as follows:

δ-lactam>aspartimide>α-lactam>aminobenzoic acid.

It is observed that the aspartimide compound is biologically more rapidly degraded, and that therefore the δ-lactam has a greater half-life; the observed potency may reflect this. A general review of β-turn structures may be found in G. B. Rose, L. M. Gierasch and J. A. Smith; Adv. Protein Chem., 1985 37 1–109.

According to a second aspect of the invention there is provided a method of solid phase synthesis of a peptide of general formula I comprising protection of the α-amino functionality of added amino acids using t-BOC or f-MOC and treating the resin-bound protected α/straight chain L-aspartyl-L-asparaginyl peptide with a base to produce the stable β-imido form of the peptide.

The base is a dialkylamine such as piperidine, or a trialkylamine, preferably triethylamine.

According to a third aspect of the invention there is provided a method of lowering the level of blood glucose in a mammal in need of such treatment, comprising administering to that animal a hypoglycaemically effective dose of a compound of general formula I. Said compound may optionally be administered together with or in conjunction with a second hypoglycaemic agent.

DETAILED DESCRIPTION OF THE INVENTION

The invention will now be described in detail by way of example only, with reference to the accompanying drawings.

EXAMPLE 1

Peptide Synthesis

The various peptide analogues of the general formula I above were synthesised either by standard solution phase synthetic procedures or by using modifications of the Merrifield solid phase peptide synthesis procedure (R. B. Merrifield, J. Amer. Chem. Soc., 85, 2149–2145, 1963), of which the following protocols are representative. Peptides were initially synthesised in the alpha/straight chain form with all amino acid side chain groups protected. For the t-BOC-synthetic approach, the α-amino functionality of the incoming amino acid was protected with the tert-butyloxycarbonyl (t-BOC) group with deprotection, following coupling, with trifluoroacetic acid in $CH_2C_2$. Side chain protecting groups such as O-benzyl, tosylbenzylester and chlorobenzyloxycarbonyl were used for the trifunctional amino acids. The initial coupling to the benzhydrylamine resin employed a 3-fold excess of the designated side chain protected amino acid $R_1$, dissolved in N,N'-dimethylformamide (DMF). Subsequent couplings of the second, third, . . . eighth amino acid (counting asp and asn separately) employed a 2 fold excess of side chain protected amino acid in DMF. The amino acids were sequentially activated using tert-butanol and dicyclohexylcarbodiimide in approximately 5 ml DMF and allowing reactants to stir at room temperature for 5–10 min. The acylurea was removed by filtration and the asymmetrical anhydride added to the resin. The suspended resin was stirred at room temperature for reaction times generally between 60 and 120 min. Each coupling was monitored for unreacted amino groups using 2,4,6-trinitrobenzenesulphonic acid. Similar synthetic strategies with the symmetrical protected amino acid anhydrides or the pentachlorophenylesters led to the preparation of identical products but in different yields. After the final coupling reaction was completed, the fully protected resin-bound peptide was treated with a reagent grade trialkylamine such as triethylamine (15–20 ml per g resin) in order to convert the-L-aspartyl-L-asparaginyl moiety to the stable β-imido form. The resin-bound peptide was side chain deprotected with trifluoroacetic acid, and the deprotected β-imido-L-aspartyl-L-asparaginyl peptide analogue cleaved from the resin using liquid hydrogen fluoride as the acid and dimethylsulphide/p-cresol or thioanisole as the scavenger. Reaction times were between 30 and 120 min at 0° C. Workup following cleavage involved standard procedures of peptide synthesis. The deprotected peptide was removed from the resin by washing with trifluoroacetic acid, then water, then water/acetonitrile mixtures.

The washes were then combined and lyophilised.

The crude dried product was chromatographed by anion exchange chromatography on Whatman DE 52 and then desalted on Biogel P2 gels. Further purification was achieved using reversed phase HPLC with octadecylsilica as stationary phase and gradients of 0–75% water-acetonitrile—0.1% trifluoroacetic acid as mobile phase.

A similar synthetic strategy using $f_{13}MOC$ (9-fluorenylmethyloxycarbonyl group) protection has also been employed.

The synthetic peptides were characterised by amino acid compositional analysis, analytical reversed phase HPLC with several elution systems, fast atom bombardment mass spectroscopy (FAB-MS), paper electrophoresis at pH6.0, FTIR-infrared spectroscopy, aminopeptidase M cleavage, $H^1$-NMR spectroscopy and circular dichroism (CD) spectroscopy.

It was found that the synthesis protocol could be manipulated in order to produce all α or all imide form of the peptide. In the absence of alkylamine treatment, all α was formed, and vice versa.

Representative results from these characterizations are illustrated for the peptide leu-ser-arg-leu-phe-asp-asn-ala (α-form, inactive), and for the peptide leu-ser-arg-leu-phe-β-imidoasp-asn-ala (β-imido form I, active).

Table 1 shows representative results of amino acid composition analysis following acid hydrolysis and aminopeptidase M cleavage.

TABLE 1

| Amino Acid Sequence | Leu | Ser | Arg | Leu | Phe | Asp | Asn | Ala |
|---|---|---|---|---|---|---|---|---|
| α-form Acid Hydrolysis[a] | 1.03 | 0.78 | 0.93 | 1.03 | 0.98 | 0.98 | 0.98 | 0.96 |

TABLE 1-continued

| Amino Acid Sequence | Leu | Ser | Arg | Leu | Phe | Asp | Asn | Ala |
|---|---|---|---|---|---|---|---|---|
| Enzymic Hydrolysis[b] | 1.02 | 0.98 | — | 1.02 | 0.98 | 0.98 | 0.92 | 1.00 |
| aspartimide Acid Hydrolysis[a] | 1.02 | 0.86 | 0.86 | 1.02 | 0.97 | 0.99 | 0.99 | 1.00 |
| Enzymic Hydrolysis[b] | 1.06 | 0.99 | — | 1.06 | 1.00 | — | — | — |

[a]) 24 h acid hydrolysis at 110° C. in 6M HCl.
[b]) 24 h aminopeptidase M digestion.

Results of circular dichroism spectroscopy, infra-red spectroscopy, FAB-MS, and $^1$H-NMR spectroscopy are illustrated in FIGS. 2 to 6 respectively. Without wishing to be bound by any proposed mechanism for the observed effects, it appears that the α form is in an extended configuration, while the β-aspartimido form I has one completely hydrophobic face, with the β-imido group at 90° to this hydrophobic face.

This conclusion is in accord with results obtained from correlation Overhauser spectroscopy (COSY) and nuclear Overhauser enhanced spectroscopy (NOESY) NMR spectroscopy for all cases of the representative active β-imide analogues.

FIG. 8 shows results of reversed phase HPLC on ODS-silica with shallow gradients of 0.1% trifluoroacetic acid -acetonitrile-water.

EXAMPLE 2

Biological Activities

Considering the physiology of hypoglycaemia and the possible molecular actions of peptide analogues with hypoglycaemic and insulin potentiating properties, the following in vitro and in vivo assays were chosen to assess the potency of the various synthetic β-imido-L-aspartyl-L-asparaginyl peptide analogues.

(a) In vitro bioassays (i) Activation of glycogen synthase
(ii) $CO_2$ production from $U^{14}C$-glucose and $^{14}C$-pyruvate via pyruvate dehydrogenase
(iii) Glucose uptake In these assays collagenase-dispersed rat adipocytes, cultured muscle cells (L6 rat skeletal muscle cell line) and hemidiaphragm preparations were employed.

(b) In vivo bioassays (i) Effect on basal blood glucose levels
(ii) Effect on insulin release
(iii) Intravenous insulin tolerance test
(iv) Activation of glycogen synthase Representative data on the biological properties of the active β-imidoaspartylasparaginyl form I peptides and their inactive α-form peptide analogues are presented.

Table 2 shows the decrease in blood glucose level in rats following intravenous injection of peptides according to the invention. Injection of the α-form had no significant effect; however, injection of the βimide form of Pep (6-13) or Pep (6-15) resulted in a significant hypoglycaemic effect.

TABLE 2

| Peptide | Conc. of Peptide μmol/100 g | No. of animals | Decrease in blood glucose from basal levels | Difference from control means | 2P Value t-test |
|---|---|---|---|---|---|
| Control | — | 28 | 1.05 | | |
| Pep (6-11) | 0.5 | 5 | 1.28 | 0.23 | N.S. |
| Pep (6-12) | 0.5 | 5 | 1.00 | −0.05 | N.S. |
| Pep (6-13) | 0.5 | 14 | 1.05 | 0.00 | N.S. |
| Pep (6-13) imide | 0.5 | 22 | 1.90 | 0.85 | <0.001 |
| Pep (6-15) | 0.5 | 5 | 1.26 | 0.21 | N.S. |
| Pep (6-15) imide | 0.5 | 5 | 2.00 | 0.95 | <0.001 |
| Pep (9-13) | 0.5 | 7 | 1.12 | 0.07 | N.S. |
| Pep (9-13) imide | 0.5 | 9 | 1.30 | 0.25 | N.S. |

Values are changes (means ±SEM) of blood glucose from the basal level (4.0–4.4 mmol glucose/l) at time 0. Differences between the control and test groups were statistically evaluated according to Student's t-test. N.S. indicates 2P>0.05.

Figure 7A:
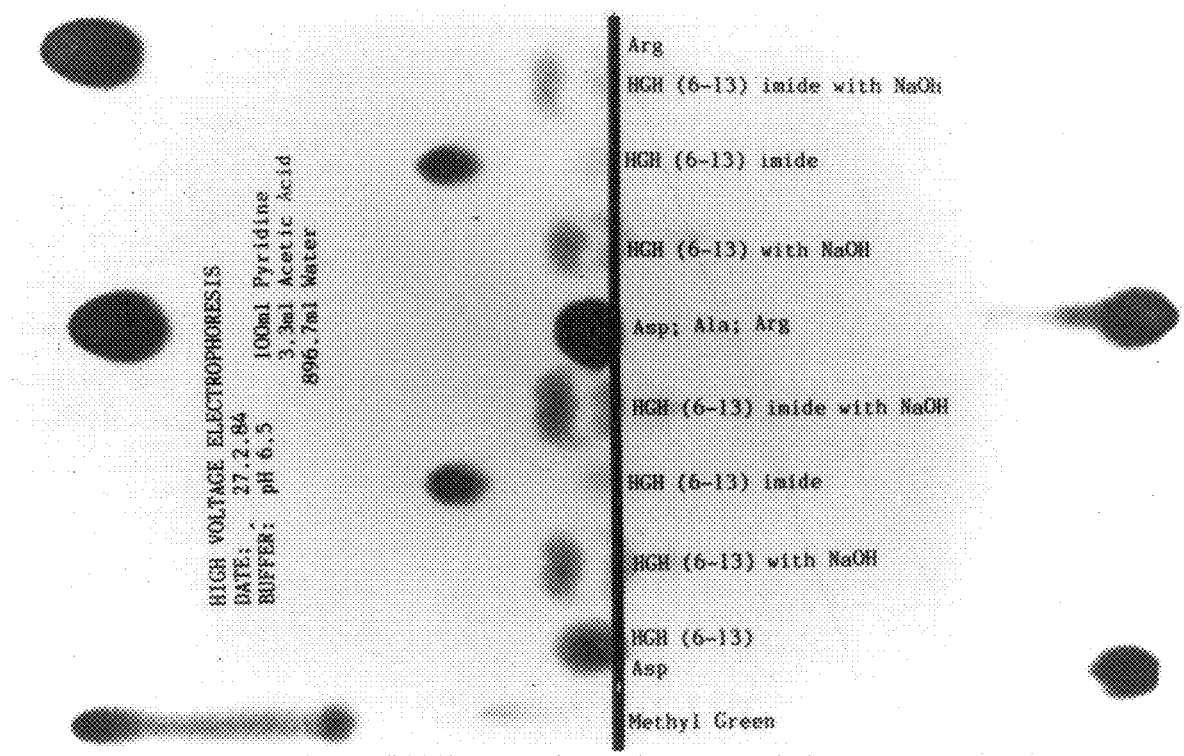
FIG. 7 represents paper electrophoresis comparing synthetic peptide β-aspartimido form I Pep (6-13) active and synthetic peptide α-form dissolved in water and dilute (1M) NaOH.
Figure 7B:
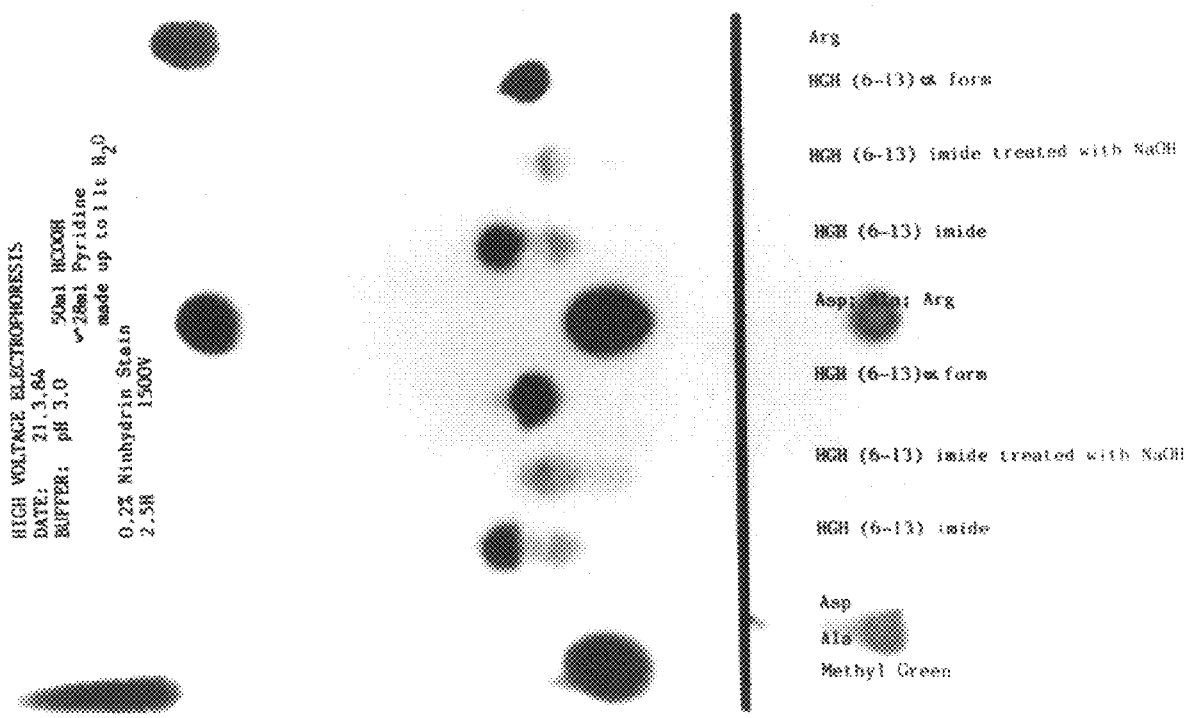

Similar results are illustrated graphically in FIG. 7. The α form of Pep (6-13) was inactive for several variants tested ($Ala^{11}$, $Gly^{10}$, $Gly^{10}Pro^{11}$, $Pro^{11}$, $Tyr^{10}$) whereas the β imide form was always active. Similarly Pep (6-11), Pep (6-12), Pep (6-13), Pep (6-15) were active only in the β imide form. However, for Pep (9-13) neither the α form nor the β imide form was active in this test.

The β imide form of peptides according to the invention was also found to potentiate the action of insulin during intravenous insulin sensitivity tests carried out on rats trained to eat on a scheduled time basis. Rats were anaesthetised with pentobarbitone, and blood samples taken at various times after intravenous infusion of insulin. Control animals were untreated or were given insulin only; test animals received insulin plus the β imide form of Pep (6-13). The results are shown in FIG. 10. The effect depended on the dose of peptide.

FIG. 11 shows that Pep (6-13) β imide accelerates the return of blood glucose levels in rats to basal level in the glucose tolerance test. The dose of Pep (6-13) was 200 μg/Kg body weight. Similarly, various forms of the peptide according to the invention in its β imide form potentiate the hypoglycaemic effect of insulin on untreated male and female mice. The effect on treated male mice trained to feed on schedule as described above was less striking, but still significant in some cases. These results are illustrated in FIGS. 12 and 13.

As well as showing activity in the in vitro assays described above, peptides according to the invention showed hypoglycaemic activity in in vitro bioassays. Table 3 shows the effect of Pep (6-13) on glycogen deposition by isolated rat hemidiaphragms. There was not effect on the basal level in the absence of added insulin. At low or high insulin concentrations ($10^2$ and $10^4$ μU/ml) respectively, Pep (6-13)β imide significantly increased glycogen deposition. The α form and the ring opened, hydrolysed β imide form were both inactive.

TABLE 3

In Vitro Effect of Pep (6–13) Imide on Glycogen Deposition
In Rat Hemidiaphragms.

| | Insulin Conc. ($\mu$U/ml) | Peptide Conc. ($\mu$mol/ml) | No. of hemidiaghragms | $^{14}$C - glycogen deposition ($\mu$mol/g) Mean ± SEM | Difference from controls | P(Student t - test) | P(Wilcoxon Rank Sum Test) |
|---|---|---|---|---|---|---|---|
| Basal | 0 | 0.1 | 14 | 2.16 ± 0.24 | 0.29 | NS | NS |
| Pep (6–13) aspartimide | | | 14 | 2.45 ± 0.19 | | | |
| Basal | 0 | 0.1 | 12 | 2.57 ± 0.23 | −0.27 | NS | NS |
| Pep (6–13). | | | 12 | 2.30 ± 0.17 | | | |
| Basal | 0 | 0.1 | 13 | 2.42 ± 0.19 | −0.02 | NS | NS |
| Pep (6–13) imide hyd | | | 12 | 2.40 ± 0.24 | | | |
| Low | $10^2$ | 0.1 | 14 | 2.75 ± 0.15 | 0.72 | 0.01 | Sig |
| Pep (6–13) aspartimide | | | 12 | 3.47 ± 0.21 | | | |
| Low | $10^2$ | 0.1 | 13 | 2.67 ± 0.14 | −0.32 | NS | NS |
| Pep (6–13). | | | 13 | 2.35 ± 0.15 | | | |
| Low | $10^2$ | 0.1 | 11 | 2.71 ± 0.15 | −0.33 | NS | NS |
| Pep (6–13) imide hyd | | | 13 | 2.38 ± 0.13 | | | |
| HIGH | $10^4$ | 0.1 | 13 | 5.53 ± 0.32 | −0.48 | 0.05 | Sig |
| Pep (6–13) aspartimide | | | 14 | 6.01 ± 0.54 | | | |
| HIGH | $10^4$ | 0.1 | 12 | 4.00 ± 0.30 | 0.36 | NS | NS |
| Pep (6–13). | | | 13 | 4.36 ± 0.46 | | | |
| HIGH | $10^4$ | 0.1 | 13 | 4.62 ± 0.66 | −0.52 | NS | NS |
| Pep (6–13) imide hyd | | | 14 | 4.10 ± 0.57 | | | | imide hyd = hydrolysed β imide form i.e. inactive ring opened form.

The β imide form of the peptide also stimulated metabolism of glucose by isolated rat adipocytes, both in the presence and in the absence of added insulin. This is shown in FIG. 14. The degree of stimulation depended on insulin dose. The dose of peptide was 10 $\mu$g per 3 ml culture.

The effect of the β imide form peptides on glucose metabolism is further shown by their ability to stimulate glucose uptake and glycogen synthesis by cultured muscle cells and isolated rat hemidiaphragms.

The results are presented in Tables 4 and 5.

TABLE 4

In Vitro Effect of β-Imido Linked L-Aspartyl-L-Asparaginyl Peptides
On Glucose Uptake In Rat Hemidiaphragms.

| | | Peptide | Glucose Uptake ($\mu$mol/g muscle/h) | | | |
|---|---|---|---|---|---|---|
| Peptide | No. of Pairs | concentration ($\mu$mol/ml) | Control Mean ± SEM | +Peptide Mean ± SEM | Mean Difference | P |
| 1–15 | 12 | 0.14 | 22.06 ± 1.39 | 39.39 ± 1.72 | 8.33 ± 1.50 | <0.001 |
| 6–13 | 15 | 0.16 | 35.34 ± 1.54 | 38.49 ± 1.53 | 3.15 ± 0.75 | <0.001 |
| 7–13 | 9 | 0.22 | 42.16 ± 1.88 | 46.79 ± 1.10 | 4.64 ± 1.63 | <0.25 |
| 8–13 | 7 | 0.20 | 38.70 ± 0.77 | 44.11 ± 0.69 | 5.41 ± 0.65 | <0.001 |
| 9–13 | 8 | 0.20 | 31.50 ± 1.01 | 32.16 ± 0.97 | 0.68 ± 0.80 | nsd |
| 10–13 | 9 | 0.20 | 33.06 ± 1.19 | 33.07 ± 1.01 | 0.80 ± 1.16 | nsd |

TABLE 5

Results of Cultured Cell Assays for the Stimulation of
Glucose Uptake by Synthetic Peptides (10 $\mu$g/ml)

| Peptide | Rate of Increase from Basal ($\mu$mol glucose/hour) |
|---|---|
| P015 Ser—Arg—Leu—Phe—Asp—Asn—Ala | 1.5 |
| P051 Leu—Ser—Arg—Leu—Phe—Asp—Asn—Ala | 3.3 |
| P057 Leu—Ser—Arg—Leu—dPhe—Asp—Asn—Ala | 2.0 |
| P063 Leu—Ser—Arg—Leu—Phe—Asp—Asn—Ala—Gly | 1.9 |

TABLE 5-continued

| | | |
|---|---|---|
| P086 | Leu—Ser—Arg—Val—Phe—Asp—Asn—Ala | 4.9 |
| P168 | Cys—Tyr—Leu—Ser—Arg—Leu—Phe—Asp—Asn—Ala | 4.0 |
| P202 | Cys—Tyr—Leu—Ser—Arg—Leu—Phe—Asp—Asn—Ala | 1.9 |

Results of Isolated Muscle Assays for the Stimulation of
Glycogen Synthesis by Synthetic Peptides (100 µg/ml)

| Peptide | | Rate of Increase from Basal (µmol glycogen/g tissue/h) |
|---|---|---|
| P051 | Leu—Ser—Arg—Leu—Phe—Asp—Asn—Ala | 0.74 |
| P076 | Leu—Ser—Arg—Leu—Phe—Asp—Gln—Ala | 0.30 |
| P078 | Leu—Ser—Arg—Leu—His—Asp—Asn—Ala | 0.11 |
| P087 | Leu—Ser—Arg—Ile—Phe—Asp—Asn—Ala | 0.36 |
| P090 | Leu—Ser—Lys—Leu—Phe—Asp—Asn—Ala | 0.16 |
| P197 | Cys—Tyr—Leu—Ser—Arg—Leu—Phe—Asp—Asn—Asn | 0.17 |
| P202 | Cys—Tyr—Leu—Ser—Arg—Leu—Phe—Asp—Asn—Ala | 0.44 |

Of the peptides tested, Pep (1-15), (6-13), and (8-13) showed a highly significant stimulation; Pep (7-13) was on the borderline of significance, while Pep (9-13) and Pep (10-13) showed no effect.

The results show that peptides of general formula I induce in a dose dependent manner a significant lowering of blood glucose levels at or below the level of 10 µM/Kg body weight with the intravenous insulin tolerance test, and enhance in a dose dependent manner glucose utilisation via activation of glycogen synthase, incorporation of glucose into glycogen and oxidation of glucose via pyruvate to carbon dioxide. A dose of as little as 0.05 µM/Kg body weight was effective with some peptides.

EXAMPLE 3

Biological Activity Of A v-Lactam Peptide Analogue

The v-lactam analogue of hGH[6-13], v-lactam$^{11-}$ hGH [6-13], was synthesized as described above. Its structure is illustrated in FIG. 15. The in vivo effect of this analogue on blood glucose levels during intravenous insulin tolerance tests in rats was examined. The peptide analogue was administered at a dose of 5 mg/Kg body weight, and removal of blood glucose during intravenous insulin tolerance tests was compared between treated animals and animals given saline. Results are illustrated in FIG. 17. A significant difference between the groups was observed at 5 mins ($P<0.05$), 45 mins ($P<0.001$), 15 mins ($P<0.005$), 30 mins ($P<0.005$), 10 mins ($P<0.005$), 60 mins ($P<0.005$) and 90 mins ($P<0.01$) after the commencement of the test. The numbers of animals studied in each group are indicated in parenthesis (n), and the results are expressed as mean±standard error of the mean.

The in vivo effect of the v-lactam$^{11}$hGH[6-13] peptide analogue on glucose incorporation into glycogen in rat diaphragm muscles was also tested, and the results are shown in FIG. 17. Anesthetized rats were injected intravenously with v-lactam$^{11}$hGH[6-13] (3 mg/Kg body weight), or an equivalent volume of saline (controls). After 30 mins, the diaphragm muscles were removed, and incubated with 0.03 µCi/µmole D-[U$^{14}$C] glucose at 37° C. for 60 mins in the absence or presence of 1.0 mU/Ml insulin. The differences between the control and test groups are statistically significant both in the absence ($P<0.025$) and the presence ($P<0.05$) of insulin. Results are the mean±standard error of the mean for groups of 5 animals.

APPLICATIONS OF THE INVENTION

The β-imido-L-aspartyl-L-asparaginyl peptides of general formula I induce
  (a) dose-dependent lowering of-blood glucose and a potentiation of glycogen synthesis in vivo
  (b) dose-dependent oxidation of glucose and the activation of glycogen synthase in vitro.

This suggests that the β-imido-L-aspartyl-L-asparaginyl peptide analogues are potent hypoglycaemic agents, and may be useful as therapeutic agents for the control of glucose metabolism, since normalisation of blood glucose levels in insulin-independent diabetes mellitus (Type II) mammals with glucose intolerance and insulin resistance is achieved by control of carbohydrate metabolism via glucose utilisation, and since glucose utilisation can be achieved via two pathways, namely oxidation of glucose or incorporation of glucose into glycogen.

Since potentiation of insulin action results in an decreased requirement for endogenous insulin, the use of the β-imido-L-aspartyl-L-asparaginyl peptide analogues may permit control of hyperinsulinaemia in insulin-independent Type II diabetes in humans or streptozotocin-treated animals.

(f) By analogy, the use of other synthetic peptide analogues containing the β-imido-L-aspartyl-L-asparaginyl moiety of general formula I is likely to exhibit either agonistic or antagonistic properties in vitro or in vivo related to glucose utilisation and so provide methods for control of hypoglycaemia or hyperglycaemia, depending on their respective agonistic or antagonistic properties in control of glucose metabolism.

It will be clearly understood that the invention in its general aspects is not limited to the specific details referred to hereinabove.

The following words used hereinabove are trade marks: BIOGEL, NUJOL.

We claim:

1. A compound of Formula I:

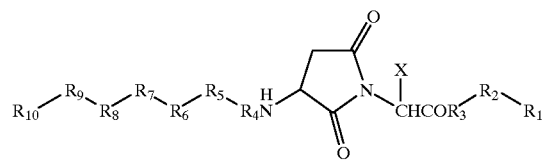

wherein X is hydrogen, —$CH_2CONH_2$ or —$CH_2CH_2CONH_2$;
  each of $R_1$, $R_2$, and $R_3$ is independently an L-α-amino acid selected from the group consisting of alanine, glycine, and phenylalanine; a δ-amino acid or an ε-amino acid;

$R_4$ is an L or D α-amino acid, a δ-amino acid or an ε-amino acid;

each of $R_5$ to $R_{10}$ is independently hydrogen or an L or D α-amino acid, a δ-amino acid or an ε-amino acid, wherein one or more of $R_1$ or $R_2$ may be absent and wherein one or more of $R_5$, $R_6$, $R_7$, $R_8$, $R_9$ or $R_{10}$ may be absent, with the proviso that only the outermost R substitution chosen from $R_5$ to $R_{10}$ can be H;

and wherein at least one of the following must exist;

$R_4$ is selected from the group consisting of L-phenylalanine, L-tyrosine, L-tryptophan, and L-histidine;

$R_5$ is selected from the group consisting of L- or D-leucine, isoleucine, and histidine;

$R_6$ is selected from the group consisting of L- or D-arginine, lysine, and histidine;

$R_7$ is a hydrophobic amino acid;

$R_7$ is selected from the group consisting of L- or D-serine, leucine, and isoleucine;

$R_8$ is selected from the group consisting of L- or D-leucine, phenylalanine, proline, isoleucine;

$R_8$ is selected from the group consisting of 6-aminohexanoic acid, 4-aminocyclohexane-1-carboxylic acid;

each of $R_9$ and $R_{10}$ is a hydrophobic amino acid; and each $R_9$ and $R_{10}$ are independently selected from the group consisting of L- or D- leucine, phenylalanine, proline, isoleucine and tyrosine;

wherein the cyclic imide structure in general formula I is a type II' β-turn structure;

or a pharmaceutically acceptable salt thereof.

2. A compound according to claim 1 in which $R_5$ is a L or D α-amino acid, a δ-amino acid or an ε-amino acid.

3. A compound according to claim 1 in which each of $R_1$, $R_2$ and $R_3$ is selected from the group consisting of alanine, glycine and phenylalanine.

4. A compound according to claim 1, in which $R_4$ is a hydrophobic amino acid.

5. A compound according to claim 4 in which $R_4$ is selected from the group consisting of L-phenylalanine, L-tyrosine, L-tryptophan and L-histidine.

6. A compound according to claim 1, in which $R_5$ is a hydrophobic amino acid.

7. A compound according to claim 6 in which $R_5$ is selected from the group consisting of L- or D- leucine, isoleucine and histidine.

8. A compound according to claim 1, in which $R_6$ is a basic amino acid.

9. A compound according to claim 8, in which $R_6$ is selected from the group consisting of L- or D- arginine, lysine, and histidine.

10. A compound according to claim 1, in which $R_7$ is a hydrophobic amino acid.

11. A compound according to claim 10 in which $R_7$ is selected from the group consisting of L- or D- serine, leucine and isoleucine.

12. A compound according to claim 1, in which $R_8$ is selected from the group consisting of L- or D- leucine, phenylalanine, proline or isoleucine, or an ε-amino acid.

13. A compound according to claim 1, in which each of $R_9$ and $R_{10}$ is a hydrophobic amino acid.

14. A compound according to claim 13, in which each of $R_9$ and $R^{10}$ is selected from the group consisting of L- or D-leucine, phenylalanine, proline, isoleucine or tyrosine.

15. A compound according to claim 1, in which one of $R_8$, $R_9$ or $R_{10}$ is coupled to $R_1$ via a bifunctional agent.

16. A compound according to claim 15, in which the bifunctional agent is 6-aminohexanoic acid.

17. A compound according to claim 1, in which $R_1$, $R_2$, $R_8$, $R_9$, or $R_{10}$ is absent from the peptide, allowing coupling between C-terminal and N-terminal amino acids via a bifunctional agent.

18. A pharmacologically active analogue or derivative of a compound according to claim 1, in which the aspartimide ring is replaced by a group selected from o-aminobenzoic acid, m-aminobenzoic acid, p-aminobenzoic acid, α-lactams and δ-lactams.

19. A pharmaceutical composition comprising a compound according to claim 1, together with a pharmaceutically acceptable carrier, diluent or excipient.

20. A compound according to claim 12, wherein $R_8$ is 6-aminohexanoic acid or 4-aminocyclohexane-1-carboxylic acid.

21. A compound according to claim 17, wherein the bifunctional agent is 6-aminohexanoic acid.

22. A compound of Formula I:

$$R_{10}\diagdown R_9\diagdown R_8\diagdown R_7\diagdown R_6\diagdown R_5\diagdown R_4N\text{H}\diagdown\text{[aspartimide]}\diagdown N(X)\text{CHCOR}_3\diagdown R_2\diagdown R_1$$

where in X is hydrogen, $-CH_2CONH_2$ or $-CH_2CH_2CONH_2$;

each of $R_1$, $R_2$, and $R_3$ is selected from the group consisting of alanine, glycine, and phenylalanine; and $R_4$ is selected from the group consisting of L-phenylalanine, L-tyrosine, L-tryptophan, and L-histidine; and $R_5$ is absent or is selected from the group consisting of H, L- or D-leucine, isoleucine, and histidine; and $R_6$ is absent or is selected from the group consisting of H, L- or D- lysine and histidine; and $R_7$ is absent or is selected from the group consisting of H, L- or D-serine, leucine, and isoleucine; and $R_8$ is absent or is selected from the group consisting of H, L- or D-leucine, phenylalanine, proline, isoleucine, 6-aminohexanoic acid, 4-aminocyclohexane-1-carboxylic acid; and each of $R_9$ and $R_{10}$ are absent or are selected from the group consisting of H, L- or D-leucine, phenylalanine, proline, isoleucine and tyrosine;

with the proviso that only the outermost R substitution chosen from $R_5$ to $R_{10}$ can be H;

or a pharmaceutically acceptable salt thereof.

23. A method of lowering the level of blood glucose in a mammal in need of such treatment, comprising administering to that animal a hypoglycaemically effective dose of a compound of general formula I,

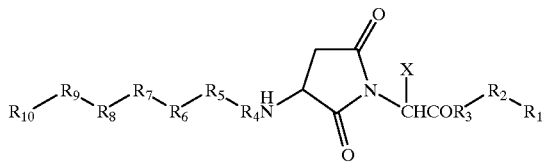
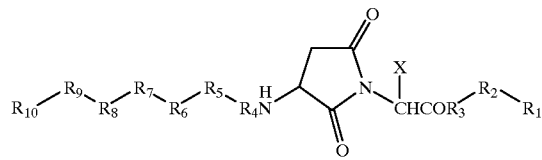

wherein X is hydrogen, —CH$_2$CONH$_2$ or —CH$_2$CH$_2$CONH$_2$;

each of R$_1$, R$_2$ and R$_3$ is an L-α-amino acid, a δ-amino acid or an ε-amino acid;

R$_4$ is an L or D α-amino acid, a δ-amino acid or an ε-amino acid; and each of R$_5$ to R$_{10}$ is independently hydrogen or an L or D α-amino acid, a δ-amino acid or an -amino acid, and wherein one or more of R$_1$, R$_2$, R$_8$, R$_9$ or R$_{10}$ may be absent, with the proviso that only the outermost R substitution chosen from R$_5$ to R$_{10}$ can be H, wherein the cyclic imide structure in general formula I is a type II' β-turn structure, or a pharmaceutically acceptable salt thereof, optionally together with or in conjunction with a second hypoglycaemic agent.

24. A method according to claim 23 in which R$_5$ is a L or D α-amino acid, a δ- amino acid or an ε-amino acid.

25. A method according to claim 23, in which each of R$_1$, R$_2$ and R$_3$ is selected from the group consisting of alanine, glycine and phenylalanine.

26. A method according to claim 23, in which R$_4$ is a hydrophobic amino acid.

27. A method according to claim 23, in which R$_4$ is selected from the group consisting of L-phenylalanine, L-tyrosine, L-tryptophan and L-histidine.

28. A method according to claim 23, in which R$_5$ is a hydrophobic amino acid.

29. A method according to claim 28, in which R$_5$ is selected from the group consisting of L- or D-leucine, isoleucine and histidine.

30. A method according to claim 23, in which R$_6$, is a basic amino acid.

31. A method according to claim 30, in with R$_6$ is selected from the group consisting of L- or D-arginine, lysine, and histidine.

32. A method according to claim 23, in which R$_7$ is a hydrophobic amino acid.

33. A method according to claim 32, in which R$_7$ is selected from the group consisting of L- or D-serine, leucine and isoleucine.

34. A method according to claim 23, in which R$_8$ is selected from the group consisting of L- or D-leucine, phenylalanine, proline or isoleucine or an ε-amino acid.

35. A method according to claim 23, in which each of R$_9$ and R$_{10}$ is a hydrophobic amino acid.

36. A method according to claim 35, in which each of R$_9$ and R$_{10}$ is selected from the group consisting of L- or D-leucine, phenylalanine, proline, isoleucine or tyrosine.

37. A pharmaceutical composition comprising a compound of Formula I:

where in X is hydrogen, —CH$_2$CONH$_2$ or —CH$_2$CH$_2$CONH$_2$;

each of R$_1$, R$_2$, and R$_3$ is independently an L -α-amino acid selected from the group consisting of alanine, glycine, and phenylalanine, a δ-amino acid or an ε-amino acid;

R$_4$ is an L or D α-amino acid, a δ-amino acid or an ε-amino acid; and each of R$_5$ to R$_{10}$ is independently hydrogen or an L or D α-amino acid, a δ-amino acid or an ε-amino acid, wherein one or more of R$_1$ or R$_2$ may be absent and wherein one or more of R$_5$, R$_6$, R$_7$, R$_8$, R$_9$, and R$_{10}$ may be absent, with the proviso that only the outermost R substitution chosen from R$_5$–R$_{10}$ can be H;

and wherein at least one of the following must exist;

R$_4$ is hydrophobic amino acid;

R$_4$ is selected from the group consisting of L-phenylalanine, L-tyrosine, L-tryptophan, and L-histidine;

R$_5$ is selected from the group consisting of L- or D-leucine, isoleucine, and histidine;

R$_7$ is a hydrophobic amino acid;

R$_7$ is selected from the group consisting of L- or D-serine, leucine, and isoleucine;

R$_8$ is selected from the group consisting of L- or D-leucine, phenylalanine, proline, isoleucine;

R$_8$ is selected from the group consisting of 6-aminohexanoic acid, 4-aminocyclohexane-1-carboxylic acid;

each of R$_9$ and R$_{10}$ is a hydrophobic amino acid; and each R$_9$ and R$_{10}$ are independently selected from the group consisting of L- or D-leucine, phenylalanine, proline, isoleucine and tyrosine;

wherein the cyclic imide structure in general formula I is a type II' β-turn structure;

or a pharmaceutically acceptable salt thereof, together with a pharmaceutically acceptable carrier, diluent or excipient.

38. A compound according to claim 1 wherein when R$_5$ is H, R$_4$ is not L-phenylalanine.

39. A compound of Formula I:

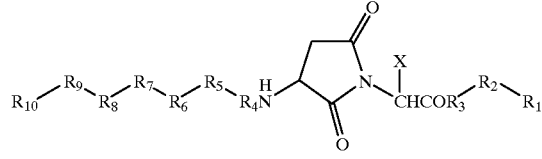

wherein R$_1$ is absent, R$_2$ is glycine, R$_3$ is alanine, X is —CH$_2$CONH$_2$, R$_4$ is phenylalanine; R$_5$ is leucine, R$_6$ is arginine, R$_7$ is serine, R$_8$ is leucine, R$_9$ is hydrogen, and R$_{10}$ is absent; or or a pharmaceutically acceptable salt thereof.

40. A method of solid phase synthesis of a peptide of claim 1, in which the peptide is bound to a resin, comprising the steps of:

(a) protecting the a-amino functionality of added amino acids using t-BOC or f-MOC,
(b) treating the resin-bound protected α/straight chain L-aspartyl-L-asparaginyl peptide with a base to produce the stable -imido form of the peptide, and
(c) recovering the peptide.

41. A method according to claim 40, in which the base is a dialkylamine or a trialkylamine.

42. A method according to claim 40, in which the base is piperidine or triethylamine.

* * * * *